US012649909B2

(12) United States Patent    (10) Patent No.:   US 12,649,909 B2
Chang et al.    (45) Date of Patent:   Jun. 9, 2026

(54) CITRATE SYNTHASE VARIANT AND METHOD FOR PRODUCING O-ACETYL-L-HOMOSERINE OR L-METHIONINE USING SAME

(71) Applicant: CJ CHEILJEDANG CORPORATION, Seoul (KR)

(72) Inventors: Jin Sook Chang, Seoul (KR); Seung Hyun Cho, Seoul (KR); Seo-Yun Kim, Seoul (KR); Jaemin Lee, Seoul (KR); Min Ji Baek, Seoul (KR); Imsang Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 323 days.

(21) Appl. No.: 18/279,519

(22) PCT Filed: Mar. 10, 2022

(86) PCT No.: PCT/KR2022/003357
§ 371 (c)(1),
(2) Date: Aug. 30, 2023

(87) PCT Pub. No.: WO2022/191633
PCT Pub. Date: Sep. 15, 2022

(65) Prior Publication Data
US 2024/0150730 A1    May 9, 2024

(30) Foreign Application Priority Data
Mar. 10, 2021   (KR) ........................ 10-2021-0031643

(51) Int. Cl.
*C12N 9/10*      (2006.01)
*C12N 15/77*     (2006.01)
*C12P 13/06*     (2006.01)
*C12P 13/12*     (2006.01)
*C12R 1/15*      (2006.01)

(52) U.S. Cl.
CPC ........... *C12N 9/1025* (2013.01); *C12N 15/77* (2013.01); *C12P 13/06* (2013.01); *C12P 13/12* (2013.01); *C12R 2001/15* (2021.05); *C12Y 203/03001* (2013.01)

(58) Field of Classification Search
CPC ...... C12N 9/1025; C12N 15/77; C12N 15/52; C12P 13/06; C12P 13/12; C12R 2001/15; C12Y 203/03001
See application file for complete search history.

(56) References Cited

U.S. PATENT DOCUMENTS

| | | |
|---|---|---|
| 7,662,943 B2 | 2/2010 | Park et al. |
| 8,283,152 B2 | 10/2012 | Kim et al. |
| 8,426,171 B2 | 4/2013 | Kim et al. |
| 10,273,491 B2 | 4/2019 | Lee et al. |
| 10,584,338 B2 | 3/2020 | Lee et al. |
| 2008/0014618 A1 | 1/2008 | Bathe et al. |

FOREIGN PATENT DOCUMENTS

| | | |
|---|---|---|
| JP | 2016-526927 A | 9/2016 |
| JP | 2018-528771 A | 10/2018 |
| KR | 10-1992-0007401 B1 | 8/1992 |
| KR | 10-1641770 B1 | 7/2016 |
| KR | 10-1915433 B1 | 11/2018 |
| KR | 10-2020-0136813 A | 12/2020 |
| WO | 2006/065095 A1 | 6/2006 |
| WO | 2016/526927 A | 8/2019 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
NCBI, GenBank accession No. WP_011013914.1 citrate synthase [Corynebacterium glutamicum] (Nov. 28, 2019).
Van Ooyen et al., "Improved L-Lysine Production With Corynebacterium glutamicum and Systemic Insight Into Citrate Synthase Flux and Activity," Biotechnology and Bioengineering, 109(8): 2070-2081 (2012).
Edelheit et al., "Simple and efficient site-directed mutagenesis using two single-primer reactions in parallel to generate mutants for protein structure-function studies," BMC Biotechnology, 9(61): 1-8 (2009).
Needleman et al., "A General Method Applicable to the Search for Similarities in the Amino Acid Sequence of Two Proteins," Journal of Molecular Biology, 48(3): 443-453 (1970).
Devereux et al., "A comprehensive set of sequence analysis programs for the VAX," Nucleic Acids Research, 12(1): 387-395 (1984).
International Search Report issued in corresponding International Patent Application No. PCT/KR2022/003357 dated Jul. 6, 2022 .
Office Action issued in corresponding Japanese Patent Application No. 2023-548892 dated Aug. 6, 2024.

* cited by examiner

*Primary Examiner* — Delia M Ramirez
(74) *Attorney, Agent, or Firm* — Morgan, Lewis & Bockius LLP

(57) ABSTRACT

The present disclosure relates to a citrate synthase variant, a microorganism comprising the variant, and a method for producing O-acetyl-L-homoserine and L-methionine using the microorganism.

20 Claims, No Drawings
Specification includes a Sequence Listing.

CITRATE SYNTHASE VARIANT AND METHOD FOR PRODUCING O-ACETYL-L-HOMOSERINE OR L-METHIONINE USING SAME

A computer readable text file, entitled "133660-04-9008-US_Sequence_Listing.txt," created on or about Aug. 28, 2023, with a file size of 42,424 bytes contains the sequence listing for this application and is hereby incorporated by reference in its entirety.

TECHNICAL FIELD

The present disclosure relates to a novel citrate synthase variant, a microorganism including the variant, and a method for producing O-acetyl-L-homoserine or L-methionine using the microorganism.

BACKGROUND ART

In order to produce L-amino acids and other beneficial substances, various researches have been carried out to develop microorganisms with high-efficiency production and technologies for fermentation processes. For example, target-specific approaches, such as a method of increasing expression of a gene encoding an enzyme involved in O-acetyl-L-homoserine biosynthesis or a method of removing a gene unnecessary for biosynthesis, have been widely used (U.S. Pat. No. 8,283,152 B2).

Meanwhile, citrate synthase (CS) is an enzyme that produces citrate by catalyzing the condensation of acetyl-CoA and oxaloacetate, which are produced during glycolysis of a microorganism, and it is also an important enzyme for determining carbon-flow into the TCA pathway.

The phenotypic changes in L-lysine-producing strains due to the deletion of gltA gene encoding citrate synthase were reported previously in a literature (Ooyen et al., Biotechnol. Bioeng., 109(8):2070-2081, 2012). However, these strains with the deletion of gltA gene have disadvantages in that not only their growth is inhibited but also their sugar consumption rates are significantly reduced thus resulting in low lysine production per unit time. Accordingly, further research is still needed that takes into account both an effective increase in L-amino acid productivity and the growth of the strains.

DISCLOSURE

Technical Problem

As a result of intensive efforts to produce O-acetyl-L-homoserine and L-methionine in high yield, the present inventors have completed this application by confirming that a novel citrate synthase variant increases O-acetyl-L-homoserine and L-methionine-producing ability.

Technical Solution

An object of the present disclosure is to provide a citrate synthase variant in which lysine, which is the amino acid corresponding to position 415 of the amino acid sequence of SEQ ID NO: 1, is substituted with histidine.

Another object of the present disclosure is to provide a polynucleotide encoding the variant of the present disclosure.

Still another object of the present disclosure is to provide a microorganism of the genus *Corynebacterium*, including the variant of the present disclosure or a polynucleotide encoding the variant.

Still another object of the present disclosure is to provide a method for producing O-acetyl-L-homoserine or L-methionine using the microorganism of the present disclosure.

Still another object of the present disclosure is to provide a composition for producing O-acetyl-L-homoserine or L-methionine, including the microorganism of the present disclosure; a medium on which the microorganism of the present disclosure is grown; or a combination thereof.

Advantageous Effects

When the citrate synthase variant of the present disclosure is used, O-acetyl-L-homoserine and L-methionine can be produced with high yield.

DETAILED DESCRIPTION OF PREFERRED EMBODIMENTS

Hereinafter, the present disclosure will be described in detail. Meanwhile, each description and embodiment disclosed herein can be applied to other descriptions and embodiments with respect to common features. That is, all combinations of various elements disclosed herein fall within the scope of the present disclosure. Further, the scope of the present disclosure is not limited by the specific description described below. In addition, a number of papers and patent documents have been referenced and cited throughout the present specification. The content of the cited papers and patent documents is incorporated herein by reference in their entirety, and the level of technical field to which the present invention belongs and the contents of the present invention will be described more clearly.

One aspect of the present disclosure provides a citrate synthase variant in which lysine, which is the amino acid corresponding to position 415 of the amino acid sequence of SEQ ID NO: 1, is substituted with histidine.

The variant of the present disclosure may be a variant, in which the amino acid corresponding to position 415 based on the amino acid sequence of SEQ ID NO: 1 in the amino acid sequence represented by SEQ ID NO: 1 is histidine, and which has a homology or identity of at least 70%, 75%, 80%, 85%, 90%, 95%, 96%, 97%, 98%, 99%, 99.5%, 99.7% or 99.9% or more to the amino acid sequence represented by SEQ ID NO: 1. For example, the variant of the present disclosure may be a variant, in which the amino acid corresponding to position 415 based on the amino acid sequence of SEQ ID NO: 1 in the amino acid sequence represented by SEQ ID NO: 1 is histidine, and may have or include an amino acid sequence having a homology or identity of at least 70%, 75%, 80%, 85%, 90%, 95%, 96%, 97%, 98%, 99%, 99.5%, 99.7% or 99.9% or more to the amino acid sequence represented by SEQ ID NO: 1, or may consist of or consist essentially of the amino acid sequence. Additionally, it is apparent that any variant having an amino acid sequence, in which part of the sequence is deleted, modified, substituted, conservatively substituted or added, may also fall within the scope of the present disclosure as long as the amino acid sequence has such a homology or identity and exhibits an efficacy corresponding to that of the variant of the present disclosure.

For example, it may be a case where the N-terminus, C-terminus and/or inside of the amino acid sequence is added or deleted with a sequence that does not alter the function of the variant of the present disclosure, a naturally occurring mutation, a silent mutation, or a conservative substitution.

As used herein, the term "conservative substitution" refers to substitution of an amino acid with another amino acid having similar structural and/or chemical properties. Such amino acid substitution may generally occur based on similarity of polarity, charge, solubility, hydrophobicity, hydrophilicity, and/or amphipathic nature of a residue. Typically, conservative substitutions may have little or no effect on the activity of the protein or polypeptide.

As used herein, the term "variant" refers to a polypeptide having one or more amino acids different from the amino acid sequence of the variant before mutation by conservative substitutions and/or modifications such that the functions and properties of the polypeptide are retained. Such variants may generally be identified by modifying one or more of the above amino acid sequences of the polypeptide and evaluating the properties of the modified polypeptide. That is, the ability of the variants may be enhanced, unchanged or reduced relative to a polypeptide before mutation. Additionally, some variants may include those in which one or more regions, such as an N-terminal leader sequence or transmembrane domain, have been removed. Further, other variants may include those in which a region has been removed from the N- and/or C-terminal of a mature protein. The term "variant" may be used interchangeably with terms such as modification, modified polypeptide, modified protein, mutant, mutein, divergent, etc., as long as the terms are used to indicate mutation. For the purpose of the present disclosure, the variant may be a variant in which lysine (Lys, K), which is the amino acid corresponding to position 415 of the amino acid sequence of SEQ ID NO: 1, is substituted with histidine (His, H).

Additionally, the variants may also include deletion or addition of amino acids that have minimal influence on the properties and secondary structure of a polypeptide. For example, the variants may be conjugated with a signal (or leader) sequence at the N-terminal involved in the translocation of proteins co-translationally or post-translationally. Further, the variants may also be conjugated with another sequence or linker to identify, purify, or synthesize the polypeptide.

As used herein, the term 'homology' or 'identity' refers to a degree of relevance between two given amino acid sequences or nucleotide sequences, and may be expressed as a percentage. The terms homology and identity may often be used interchangeably with each other.

The sequence homology or identity of conserved polynucleotides or polypeptides may be determined by standard alignment algorithms and can be used with a default gap penalty established by the program being used. Substantially, homologous or identical sequences are generally expected to hybridize to all or part of the sequences under moderate or high stringent conditions. It is apparent that hybridization with polynucleotides containing general codon or degenerate codons in hybridizing polynucleotides is also included.

Whether any two polynucleotide or polypeptide sequences have a homology, similarity, or identity may be, for example, determined by a known computer algorithm such as the "FASTA" program (Pearson et al., (1988) [Proc. Natl. Acad. Sci. USA 85]: 2444) using default parameters. Alternatively, it may be determined by the Needleman-Wunsch algorithm (Needleman and Wunsch, 1970, J. Mol. Biol. 48: 443-453), which is performed using the Needleman program of the EMBOSS package (EMBOSS: The European Molecular Biology Open Software Suite, Rice et al., 2000, Trends Genet. 16: 276-277) (preferably, version 5.0.0 or versions thereafter) (GCG program package (Devereux, J., et al., Nucleic Acids Research 12: 387 (1984)), BLASTP, BLASTN, FASTA (Atschul, [S.] [F.,] [ET AL.], J MOLEC BIOL 215]: 403 (1990); Guide to Huge Computers, Martin J. Bishop, [ED.,] Academic Press, San Diego, 1994, and [CARILLO ET AL.](1988) SIAM J Applied Math 48: 1073). For example, the homology, similarity, or identity may be determined using BLAST or ClustalW of the National Center for Biotechnology Information (NCBI).

The homology, similarity, or identity of polynucleotides or polypeptides may be, for example, determined by comparing sequence information using, for example, the GAP computer program, such as Needleman et al. (1970), J Mol Biol. 48: 443 as disclosed in Smith and Waterman, Adv. Appl. Math (1981) 2:482. In summary, the GAP program defines the homology, similarity, or identity as the value obtained by dividing the number of similarly aligned symbols (i.e., nucleotides or amino acids) by the total number of the symbols in the shorter of the two sequences. Default parameters for the GAP program may include (1) a binary comparison matrix (containing a value of 1 for identities and 0 for non-identities) and the weighted comparison matrix of Gribskov et al. (1986), Nucl. Acids Res. 14:6745, as disclosed in Schwartz and Dayhoff, eds., Atlas of Protein Sequence and Structure, National Biomedical Research Foundation, pp. 353-358 (1979) (or EDNAFULL substitution matrix (EMBOSS version of NCBI NUC4.4)); (2) a penalty of 3.0 for each gap and an additional 0.10 penalty for each symbol in each gap (or a gap opening penalty of 10 and a gap extension penalty of 0.5); and (3) no penalty for end gaps.

As used herein, the term "corresponding to" refers to an amino acid residue at the position recited in a peptide, or an amino acid residue which is similar, identical, or homologous to the residue recited in a peptide. Identifying an amino acid at a corresponding position may be determining a particular amino acid in a sequence that refers to a particular sequence. As used herein, the "corresponding region" generally refers to a similar or corresponding position in the related protein or reference protein.

For example, any amino acid sequence is aligned with SEQ ID NO: 1, and based on the alignment, each amino acid residue of the amino acid sequence can be numbered with reference to the numerical position of the amino acid residue corresponding to the amino acid residue of SEQ ID NO: 1. For example, a sequence alignment algorithm such as that described herein can identify the position of an amino acid or a position where modifications such as substitutions, insertions or deletions occur compared to a query sequence (also referred to as a "reference sequence").

Example of the alignment may be determined by the Needleman-Wunsch algorithm (Needleman and Wunsch, 1970, J. Mol. Biol. 48: 443-453), which is performed using the Needleman program of the EMBOSS package (EMBOSS: The European Molecular Biology Open Software Suite, Rice et al., 2000, Trends Genet. 16: 276-277), etc., but is not limited thereto, and sequence alignment programs, such as pairwise sequence comparison algorithms, etc., known in the art may be appropriately used.

As used herein, the term "citrate synthase" refers to an enzyme that produces citrate by catalyzing the condensation of acetyl-CoA and oxaloacetate, which are produced during the glycolysis of a microorganism. Additionally, the citrate synthase catalyzes the condensation reaction of a two-carbon acetate residue from acetyl-CoA and a molecule of 4-carbon oxaloacetate to form a 6-carbon citrate. The term "citrate synthase" may be used interchangeably with "enzyme for synthesizing citrate", "CS", "GltA protein", or "GltA". In the present disclosure, the sequence of the GltA can be obtained from NCBI's GenBank, a known database. In addition, the GltA may be a polypeptide having citrate synthase activity encoded by the gltA gene, but is not limited thereto.

The variant of the present disclosure may have an activity of increasing O-acetyl-L-homoserine or L-methionine-producing ability compared to a wild-type polypeptide The variant of the present disclosure may be a citrate synthase variant in which asparagine, which is the amino acid corresponding to position 241 of the amino acid sequence of SEQ ID NO: 1, is substituted with threonine.

The variant of the present disclosure may be a variant, in which the amino acid corresponding to position 241 based on the amino acid sequence of SEQ ID NO: 1 in the amino acid sequence represented by SEQ ID NO: 1 is threonine, and which has a homology or identity of at least 70%, 75%, 80%, 85%, 90%, 95%, 96%, 97%, 98%, 99%, 99.5%, 99.7% or 99.9% or more to the amino acid sequence represented by SEQ ID NO: 1. For example, the variant of the present disclosure may be a variant, in which the amino acid corresponding to position 241 based on the amino acid sequence of SEQ ID NO: 1 in the amino acid sequence represented by SEQ ID NO: 1 is histidine, and may have or include an amino acid sequence having a homology or identity of at least 70%, 75%, 80%, 85%, 90%, 95%, 96%, 97%, 98%, 99%, 99.5%, 99.7% or 99.9% or more to the amino acid sequence represented by SEQ ID NO: 1, or may consist of or consist essentially of the amino acid sequence. Additionally, it is apparent that any variant having an amino acid sequence, in which part of the sequence is deleted, modified, substituted, conservatively substituted or added, may also fall within the scope of the present disclosure as long as the amino add sequence has such a homology or identity and exhibits an efficacy corresponding to that of the variant of the present disclosure.

The variant of the present disclosure may have a sequence identity of 80% or more with the amino acid sequence of SEQ ID NO: 1.

Additionally, the variant of the present disclosure may include a polypeptide represented by the amino acid sequence of SEQ ID NO: 3. The amino acid sequence of SEQ ID NO: 3 may be an amino acid sequence in which lysine corresponding to position 415 in the amino acid sequence at position 362 to position 415 from the N-terminus of the amino acid sequence of SEQ ID NO: 1 is substituted with histidine.

The variant of the present disclosure may include the amino acid sequence of General Formula 1 below:

```
[General Formula 1]
                                    (SEQ ID NO: 33)
X₁N HGGDATX₂FMN KVKNKEDGVR LMGFGHRVYK

NYDPRAAIVK ETAHEILEHL GGDDLLDLAI KLEEIALADD

X₃FISRKLYPN VDFYTGLIYR AMGFPTDFFT VLFAIGRLPG

WIAHYREQLG AAGNH;
``` wherein in General Formula 1 above,
X₁ is asparagine or serine;
X₂ is alanine or glutamic acid; and
X₃ is tyrosine or cysteine.

6

The variant of the present disclosure may be a citrate synthase variant in which lysine, which is the amino acid corresponding to position 415 of the amino acid sequence of SEQ ID NO: 1, is substituted with histidine, and asparagine, which is the amino acid corresponding to position 241 of the amino acid sequence of SEQ ID NO: 1, is substituted with threonine.

The variant of the present disclosure may have a sequence identity of 90% or more with the amino acid sequence of SEQ ID NO: 4 or 6. Additionally, the variant of the present disclosure may include, consist of, or consist essentially of an amino acid sequence having a sequence identity of 90% or more with the amino acid sequence of SEQ ID NO: 4 or 6. For example, the variant of the present disclosure may have a sequence identity of 90%, 91%, 92%, 93%, 94%, 95%, 96%, 97%, 98%, 99%, 99.5%, or 99.7% with the amino acid sequence of SEQ ID NO: 4 or 6, may include an amino acid sequence having the sequence identity, or may consist of or essentially consist of an amino acid sequence having the sequence identity.

Another aspect of the present disclosure provides a polynucleotide encoding the variant of the present disclosure.

As used herein, the term "polynucleotide", which is a polymer of nucleotides composed of nucleotide monomers connected in a lengthy chain by a covalently bond, is a DNA or RNA strand having at least a certain length. More specifically, it may refer to a polynucleotide fragment encoding the variant.

In the polynucleotide of the present disclosure, the nucleotides corresponding to positions 1243 to 1245 based on the nucleic acid sequence of SEQ ID NO: 2 are CAC, and any polynucleotide represented by a nucleic acid sequence having a homology or identity of at least 70%, 75%, 80%, 85%, 90%, 95%, 96%, 97%, 98%, 99%, 99.5%, 99.7%, or 99.9% or more, and less than 100% with the nucleic acid sequence represented by SEQ ID NO: 2 may be included. Additionally, in the polynucleotide of the present disclosure, the nucleotides corresponding to positions 1243 to 1245 and 721 to 723 based on the nucleic acid sequence of SEQ ID NO: 2 are CAC and ACC, and any polynucleotide represented by a nucleic acid sequence having a homology or identity of at least 70%, 75%, 80%, 85%, 90%, 95%, 96%, 97%, 98%, 99%, 99.5%, 99.7%, or 99.9% or more with the nucleic acid sequence represented by SEQ ID NO: 5 or 7 may be included. Further, it is apparent that any polynucleotide represented by a nucleic acid sequence, in which part of the sequence is deleted, modified, substituted, conservatively substituted or added, may also fall within the scope of the present disclosure as long as the sequence has such a homology or identity and encodes a polypeptide or protein exhibiting an efficacy corresponding to that of the variant of the present disclosure.

The polynucleotide of the present disclosure may undergo various modifications in the coding region within the scope that does not change the amino acid sequence of the variant of the present disclosure, due to codon degeneracy or in consideration of the codons preferred in an organism in which the variant of the present disclosure is to be expressed. Here, in the sequence having the homology or identity, the codon encoding the amino acid corresponding to position 415 of SEQ ID NO: 1 may be one of the codons encoding histidine. Additionally, in the sequence having the homology or identity, the codon encoding the amino acid corresponding to position 241 of SEQ ID NO: 1 may be one of the codons encoding threonine.

Further, the polynucleotide of the present disclosure may include a probe that may be prepared from a known gene sequence, for example, any sequence which can hybridize with a sequence complementary to all or part of the polynucleotide sequence of the present disclosure under stringent conditions without limitation. The "stringent conditions" refers to conditions under which specific hybridization between polynucleotides is allowed. Such conditions are specifically described in the literature (J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York, 9.50-9.51, 11.7-11.8). For example, the stringent conditions may include conditions under which polynucleotides having a high homology or identity of 70% or more, 75% or more, 80% or more, 85% or more, 90% or more, 95% or more, 96% or more, 97% or more, 98% or more, or 99% or more are hybridized with each other and polynucleotides having a homology or identity lower than the above homologies or identities are not hybridized with each other, or washing conditions of Southern hybridization, that is, washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS.

Hybridization requires that two nucleic acids contain complementary sequences, although mismatches between bases are possible depending on the stringency of the hybridization. The term "complementary" is used to describe the relationship between nucleotide bases that can hybridize with each other. For example, with respect to DNA, adenine is complementary to thymine, and cytosine is complementary to guanine. Therefore, the polynucleotide of the present disclosure may include isolated nucleotide fragments complementary to the entire sequence as well as nucleic acid sequences substantially similar thereto.

Specifically, polynucleotides having a homology or identity with the polynucleotide of the present disclosure may be detected using the hybridization conditions including a hybridization step at a $T_m$ value of 55° C. under the above-described conditions. Further, the $T_m$ value may be 60° C., 63° C., or 65° C., but is not limited thereto, and may be appropriately adjusted by those skilled in the art depending on the purpose thereof.

The appropriate stringency for hybridizing the polynucleotides depends on the length of the polynucleotides and the degree of complementation, and these variables are well known in the art (e.g., Sambrook et al.).

In one example, the polynucleotide of the present disclosure may include a polynucleotide represented by the nucleic acid sequence at positions 1084 to 1245 based on the nucleic acid sequence of SEQ ID NO: 5, or a polynucleotide represented by the nucleic acid sequence of SEQ ID NO: 5 or 7.

In the polynucleotide of the present disclosure, the variant is as described in the other aspects above.

Still another aspect of the present disclosure provides a vector containing the polynucleotide of the present disclosure. The vector may be an expression vector for expressing the polynucleotide in a host cell, but is not limited thereto.

The vector of the present disclosure may include a DNA construct containing the nucleotide sequence of a polynucleotide encoding the target polypeptide operably linked to a suitable expression regulatory region (expression regulatory sequence) so as to be able to express the target polypeptide in a suitable host cell. The expression regulatory region may include a promoter capable of initiating transcription, any operator sequence for regulating the transcription, a sequence encoding a suitable mRNA ribosome-binding site, and a sequence for regulating termination of transcription and translation. Once transformed into a suitable host cell, the vector may replicate or function independently from the host genome, or may integrate into genome thereof.

The vector used in the present disclosure is not particularly limited, and any vector known in the art may be used. Examples of the vector typically used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, and Charon21A, etc. may be used; and as a plasmid vector, those based on pDZ, pBR, pUC, pBluescriptll, pGEM, pTZ, pCL and pET, etc. may be used. Specifically, pDZ, pDC, pDCM2, pACYC177, pACYC184, pCL, pECCG117(Biotechnology letters vol 13, No. 10, p. 721-726(1991), Korean Patent No. 10-1992-0007401), pUC19, pBR322, pMW118, pCC1BAC vector, etc. may be used.

In one example, a polynucleotide encoding a target polypeptide may be inserted into the chromosome through a vector for intracellular chromosomal insertion. The insertion of the polynucleotide into the chromosome may be performed by any method known in the art, for example, by homologous recombination, but is not limited thereto. The vector may further include a selection marker to confirm the insertion into the chromosome. The selection marker is for selecting the cells transformed with the vector, that is, for confirming whether the target nucleic acid molecule has been inserted, and markers that provide selectable phenotypes, such as drug resistance, auxotrophy, resistance to cell toxic agents, or expression of surface polypeptides, may be used. Only cells expressing the selection marker are able to survive or to show different phenotypes under the environment treated with the selective agent, and thus the transformed cells may be selected.

As used herein, the term "transformation" refers to the introduction of a vector containing a polynucleotide encoding a target polypeptide into a host cell or microorganism so that the polypeptide encoded by the polynucleotide can be expressed in the host cell. As long as the transformed polynucleotide can be expressed in the host cell, it does not matter whether the transformed polynucleotide is integrated into the chromosome of the host cell and located therein or located extra chromosomally, and both cases can be included. Further, the polynucleotide may include DNA and/or RNA encoding the target polypeptide. The polynucleotide may be introduced in any form, as long as it can be introduced into the host cell and expressed therein. For example, the polynucleotide may be introduced into the host cell in the form of an expression cassette, which is a gene construct including all elements required for its autonomous expression. The expression cassette may commonly include a promoter operably linked to the polynucleotide, a transcription terminator, a ribosome-binding site, or a translation terminator. The expression cassette may be in the form of a self-replicable expression vector. Additionally, the polynucleotide may be introduced into a host cell as it is and operably linked to sequences required for expression in the host cell, but is not limited thereto.

Further, as used herein, the term "operably linked" means that the polynucleotide sequence is functionally linked to a promoter sequence that initiates and mediates transcription of the polynucleotide encoding the target variant of the present disclosure.

In the vector of the present disclosure, the variant and polynucleotide are as described in the other aspects above.

Yet another aspect of the present disclosure provides a microorganism of the genus *Corynebacterium*, including the variant of the present disclosure or the polynucleotide of the present disclosure.

The microorganism of the present disclosure may include the variant of the present disclosure, a polynucleotide encoding the variant, or a vector containing the polynucleotide of the present disclosure.

As used herein, the term "microorganism (or strain)" includes all wild-type microorganisms, or naturally or artificially genetically modified microorganisms, and it may be a microorganism in which a particular mechanism is weakened or enhanced due to insertion of a foreign gene, or enhancement or inactivation of the activity of an endogenous gene, etc., and may be a microorganism including genetic modification to produce a desired polypeptide, protein or product.

The microorganism of the present disclosure may be a microorganism including any one or more of the variant of the present disclosure, the polynucleotide of the present disclosure, and the vector containing the polynucleotide of the present disclosure; a microorganism modified to express the variant of the present disclosure or the polynucleotide of the present disclosure; a microorganism (e.g., a recombinant strain) expressing the variant of the present disclosure or the polynucleotide of the present disclosure; or a microorganism (e.g., a recombinant strain) having the variant activity of the present disclosure, but is not limited thereto.

The microorganism of the present disclosure may be a strain having an O-acetyl-L-homoserine or L-methionine-producing ability.

The microorganism of the present disclosure may be a microorganism that naturally has a GItA, O-acetyl-L-homoserine or L-methionine-producing ability, or a microorganism that has been introduced with the variant of the present disclosure or the polynucleotide encoding the same (or the vector containing the polynucleotide) to a parent strain that does not naturally have a GItA, O-acetyl-L-homoserine or L-methionine-producing ability, and/or a microorganism that has been given a GItA, O-acetyl-L-homoserine or L-methionine-producing ability, but is not limited thereto.

In one example, the microorganism of the present disclosure is a cell or microorganism transformed with the polynucleotide of the present disclosure or a vector containing the polynucleotide of the present disclosure to express the polynucleotide of the present disclosure to express the variant of the present disclosure, and for purposes of the present disclosure, the microorganism of the present disclosure may include all microorganisms capable of producing O-acetyl-L-homoserine or L-methionine, including the variant of the present disclosure. For example, the strain of the present disclosure may be a recombinant strain whose O-acetyl-L-homoserine or L-methionine-producing ability is increased by introducing the polynucleotide encoding the variant of the present disclosure into a natural wild-type microorganism or a microorganism producing O-acetyl-L-homoserine or L-methionine. The recombinant strain with an increased O-acetyl-L-homoserine or L-methionine-producing ability may be a microorganism having an increased O-acetyl-L-homoserine or L-methionine-producing ability compared to a natural wild-type microorganism or a non-modified microorganism of citrate synthase (i.e., a microorganism expressing a wild-type protein (SEQ ID NO: 1) or a microorganism not expressing the variant of the present disclosure), but is not limited thereto. For example, the non-modified microorganism of citrate synthase, which is the target strain for comparing the increase in the O-acetyl-L-homoserine or L-methionine-producing ability, may be ATCC14067 strain, ATCC13032 strain, and ATCC13869 strain, but is not limited thereto.

In one example, the recombinant strain having an increased production ability may have an increased O-acetyl-L-homoserine or L-methionine-producing ability by about 1% or more, 5% or more, 7% or more, about 10% or more, about 20% or more, or about 30% or more (the upper limit is not particularly limited, for example, about 200% or less, about 150% or less, about 100% or less, about 50% or less, about 45% or less, about 40% or less, or about 30% or less) as compared to the O-acetyl-L-homoserine or L-methionine-producing ability of a parent strain before modification or a non-modified microorganism, but is not limited thereto, as long as it has an increased+value compared to the production ability of a parent strain before modification or a non-modified microorganism. In another example, the recombinant strain having an increased production ability may have an increased O-acetyl-L-homoserine or L-methionine-producing ability by about 1.01 times or more, about 1.05 times or more, about 1.07 times or more, about 1.1 times or more, about 1.2 times or more, or about 1.3 times or more (the upper limit is not particularly limited, for example, about 10 times or less, about 5 times or less, about 3 times or less, or about 2 times or less) as compared to that of a parent strain before modification or a non-modified microorganism.

As used herein, the term "about" refers to a range which includes all of ±0.5, ±0.4, ±0.3, ±0.2, ±0.1, etc., and includes all of the values that are equivalent or similar to those following the values, but the range is not limited thereto.

As used herein, the term "non-modified microorganism" does not exclude a strain containing a mutation that may occur naturally in a microorganism, and may refer to a wild-type strain or natural-type strain itself, or a strain before the trait is altered due to genetic modification caused by natural or artificial factors. For example, the non-modified microorganism may refer to a strain into which the protein variant described herein is not introduced, or a strain before the introduction thereof. The "non-modified microorganism" may be used interchangeably with "strain before modification", "microorganism before modification", "non-mutant strain", "non-modified strain", "non-mutant microorganism" or "reference microorganism".

In another example of the present disclosure, the microorganism of the present disclosure may be *Corynebacterium glutamicum, Corynebacterium crudilactis, Corynebacterium deserti, Corynebacterium efficiens, Corynebacterium callunae, Corynebacterium stationis, Corynebacterium singulare, Corynebacterium halotolerans, Corynebacterium striatum, Corynebacterium ammoniagenes, Corynebacterium pollutisoli, Corynebacterium imitans, Corynebacterium testudinoris*, or *Corynebacterium flavescens*.

The microorganism of the present disclosure may be a microorganism in which the NCgl2335 protein is further weakened.

Additionally, the microorganism of the present disclosure may be a microorganism in which the activity of L-methionine/branched-chain amino acid exporter (YjeH) is further enhanced.

As used herein, the term "weakening" of a polypeptide is a comprehensive concept including both reduced or no activity compared to its endogenous activity. The weakening may be used interchangeably with terms such as inactivation, deficiency, down-regulation, decrease, reduce, attenuation, etc.

The weakening may also include a case where the polypeptide activity itself is decreased or removed compared to the activity of the polypeptide originally possessed by a microorganism due to a mutation of the polynucleotide encoding the polypeptide; a case where the overall level of intracellular polypeptide activity and/or concentration (expression level) is decreased compared to a natural strain due to the inhibition of expression of the gene of the polynucleotide encoding the polypeptide, or the inhibition of translation into the polypeptide, etc.; a case where the polynucleotide is not expressed at all; and/or a case where no polypeptide activity is observed even when the polynucleotide is expressed. As used herein, the term "endogenous activity" refers to the activity of a particular polypeptide originally possessed by a parent strain before transformation, a wild-type or a non-modified microorganism, when a trait is altered through genetic modification caused by natural or artificial factors, and may be used interchangeably with "activity before modification". The expression that the polypeptide activity is "inactivated, deficient, decreased, down-regulated, reduced or attenuated" compared to its endogenous activity means that the polypeptide activity is decreased compared to the activity of a particular polypeptide originally possessed by a parent strain before transformation or a non-modified microorganism.

The weakening of the polypeptide activity can be performed by any method known in the art, but the method is not limited thereto, and can be achieved by applying various methods well known in the art (e.g., Nakashima N et al., Bacterial cellular engineering by genome editing and gene silencing. Int J Mol Sci. 2014,15(2):2773-2793, Sambrook et al. Molecular Cloning 2012, etc.).

Specifically, the weakening of the polypeptide activity of the present disclosure may be:

1) deleting a part or all of the gene encoding the polypeptide;

2) modifying the expression regulatory region (expression regulatory sequence) such that the expression of the gene encoding the polypeptide is decreased;

3) modifying the amino acid sequence constituting the polypeptide such that the polypeptide activity is removed or weakened (e.g., deletion/substitution/addition of one or more amino acids on the amino acid sequence);

4) modifying the gene sequence encoding the polypeptide such that the polypeptide activity is removed or weakened (e.g., deletion/substitution/addition of one or more of nucleotides on the nucleotide sequence of the polypeptide gene to encode a polypeptide that has been modified to remove or weaken the activity of the polypeptide);

5) modifying the nucleotide sequence encoding the initiation codon or 5'-UTR of the gene transcript encoding the polypeptide;

6) introducing an antisense oligonucleotide (e.g., antisense RNA), which binds complementary to the gene transcript encoding the polypeptide;

7) adding a sequence complementary to the Shine-Dalgarno (SD) sequence on the front end of the SD sequence of the gene encoding the polypeptide to form a secondary structure, thereby inhibiting the ribosomal attachment;

8) a reverse transcription engineering (RTE), which adds a promoter, which is to be reversely transcribed, on the 3' terminus of the open reading frame (ORF) of the gene sequence encoding the polypeptide; or 9) a combination of two or more selected from above 1) to 8), but is not particularly limited thereto.

For example,

The 1) deleting a part or all of the gene encoding the polypeptide may be deleting all of the polynucleotide encoding the endogenous target polypeptide within the chromosome, or replacing the polynucleotide with a polynucleotide having a partially deleted nucleotide, or with a marker gene.

The 2) modifying the expression regulatory region (expression regulatory sequence) may be inducing a modification on the expression regulatory region (expression regulatory sequence) through deletion, insertion, non-conservative substitution or conservative substitution, or a combination thereof; or replacing the sequence with a sequence having a weaker activity. The expression regulatory region may include a promoter, an operator sequence, a sequence encoding a ribosome-binding site, and a sequence for regulating the termination of transcription and translation, but is not limited thereto.

The 3) and 4) modifying the amino acid sequence or the polynucleotide sequence may be inducing a modification on the sequence through deletion, insertion, non-conservative or conservative substitution of the amino acid sequence of the polypeptide or the polynucleotide sequence encoding the polypeptide, or a combination thereof to weaken the activity of the polypeptide, or replacing the sequence with an amino acid sequence or a polynucleotide sequence modified to have a weaker activity, or an amino acid sequence or a polynucleotide sequence modified to have no activity, but are not limited thereto. For example, the expression of the gene may be inhibited or weakened by introducing a mutation into the polynucleotide sequence to form a termination codon, but is not limited thereto.

The 5) modifying the nucleotide sequence encoding the initiation codon or 5'-UTR of the gene transcript encoding the polypeptide may be, for example, substituting the nucleotide sequence with a nucleotide sequence encoding another initiation codon having a lower polypeptide expression rate than the endogenous initiation codon, but is not limited thereto.

The 6) introducing an antisense oligonucleotide (e.g., antisense RNA), which binds complementary to the gene transcript encoding the polypeptide, can be found in the literature [Weintraub, H. et al., Antisense-RNA as a molecular tool for genetic analysis, Reviews-Trends in Genetics, Vol. 1(1) 1986].

The 7) adding a sequence complementary to the Shine-Dalgarno (SD) sequence on the front end of the SD sequence of the gene encoding the polypeptide to form a secondary structure, thereby inhibiting the ribosome attachment may be inhibiting mRNA translation or reducing the speed thereof.

Further, the 8) reverse transcription engineering (RTE), which adds a promoter, which is to be reversely transcribed, on the 3' terminus of the open reading frame (ORF) of the gene sequence encoding the polypeptide, may be forming an antisense nucleotide complementary to the gene transcript encoding the polypeptide to weaken the activity.

As used herein, the term "enhancement" of the activity of a polypeptide means that the activity of a polypeptide is increased compared to its endogenous activity. The enhancement may be used interchangeably with terms such as activation, up-regulation, overexpression, increase, etc. In particular, the activation, enhancement, up-regulation, overexpression and increase may include both cases in which an activity not originally possessed is exhibited, or the activity is enhanced compared to the endogenous activity or the activity before modification. The "endogenous activity" refers to the activity of a particular polypeptide originally possessed by a parent strain before transformation or a non-modified microorganism, when a trait is altered through genetic modification caused by natural or artificial factors, and may be used interchangeably with "activity before modification". The "enhancement", "up-regulation", "over-expression" or "increase" in the activity of a polypeptide compared to its endogenous activity means that the activity and/or concentration (expression level) of the polypeptide is enhanced compared to that of a particular polypeptide originally possessed by a parent strain before transformation or a non-modified microorganism.

The enhancement may be achieved by introducing a foreign polypeptide, or enhancing the activity and/or concentration (expression level) of the endogenous polypeptide. The enhancement of the activity of the polypeptide can be confirmed by the increase in the level of activity of the polypeptide, expression level, or the amount of product excreted from the polypeptide.

The enhancement of the activity of the polypeptide can be applied by various methods well known in the art, and the method is not limited as long as it can enhance the activity of the target polypeptide compared to that of a microorganism before modification. Specifically, genetic engineering and/or protein engineering well known to those skilled in the art, which is a common method of molecular biology, may be used, but the method is not limited thereto (e.g., Sitnicka et al. Functional Analysis of Genes. Advances in Cell Biology. 2010, Vol. 2. 1-16, Sambrook et al. Molecular Cloning 2012, etc.).

Specifically, the enhancement of the activity of the polypeptide of the present disclosure may be:

1) increasing the intracellular copy number of a polynucleotide encoding the polypeptide;

2) replacing the expression regulatory region of a gene encoding the polypeptide on the chromosome with a sequence having a stronger activity;

3) modifying the nucleotide sequence encoding the initiation codon or 5'-UTR of the gene transcript encoding the polypeptide;

4) modifying the amino acid sequence of the polypeptide such that the activity of the polypeptide is enhanced;

5) modifying the polynucleotide sequence encoding the polypeptide such that the activity of the polypeptide is enhanced (e.g., modifying the polynucleotide sequence of the polypeptide gene to encode a polypeptide that has been modified to enhance the activity of the polypeptide);

6) introducing a foreign polypeptide exhibiting the polypeptide activity or a foreign polynucleotide encoding the same;

7) codon-optimization of the polynucleotide encoding the polypeptide;

8) analyzing the tertiary structure of the polypeptide and thereby selecting and modifying the exposed site, or chemically modifying the same; or 9) a combination of two or more selected from above 1 to 8), but is not particularly limited thereto.

More specifically,

The 1) increasing the intracellular copy number of a polynucleotide encoding the polypeptide may be introducing a vector, which is operably linked to the polynucleotide encoding the polypeptide and is able to replicate and function regardless of a host cell, into the host cell. Alternatively, it may be introducing one copy or two copies of polynucleotides encoding the polypeptide into the chromosome of a host cell. The introduction into the chromosome may be performed by introducing a vector, which is able to insert the polynucleotide into the chromosome of a host cell, into the host cell, but is not limited thereto. The vector is as described above.

The 2) replacing the expression regulatory region (or expression regulatory sequence) of a gene encoding the polypeptide on the chromosome with a sequence having a strong activity may be, for example, inducing a modification on the sequence through deletion, insertion, non-conservative or conservative substitution, or a combination thereof to further enhance the activity of the expression regulatory region, or replacing the sequence with a sequence having a stronger activity. The expression regulatory region may include, but is not particularly limited to, a promoter, an operator sequence, a sequence encoding a ribosome-binding site, and a sequence regulating the termination of transcription and translation, etc. In one example, it may be replacing the original promoter with a strong promoter, but is not limited thereto.

Examples of the known strong promoter may include CJ1 to CJ7 promoters (U.S. Pat. No. 7,662,943 B2), lac promoter, trp promoter, trc promoter, tac promoter, lambda phage PR promoter, PL promoter, tet promoter, gapA promoter, SPL7 promoter, SPL13 (sm3) promoter (U.S. Ser. No. 10/584,338 B2), 02 promoter (U.S. Ser. No. 10/273,491 B2), tkt promoter, yccA promoter, etc., but the strong promoter is not limited thereto.

The 3) modifying the nucleotide sequence encoding the initiation codon or 5'-UTR of the gene transcript encoding the polypeptide may, for example, substituting the nucleotide sequence with a nucleotide sequence encoding another initiation codon having a higher expression rate of the polypeptide compared to the endogenous initiation codon, but is not limited thereto.

The 4) and 5) modifying the amino acid sequence or the polynucleotide sequence may be inducing a modification on the sequence through deletion, insertion, non-conservative or conservative substitution of the amino acid sequence of the polypeptide or the polynucleotide sequence encoding the polypeptide, or a combination thereof to enhance the activity of the polypeptide, or replacing the sequence with an amino acid sequence or a polynucleotide sequence modified to have a stronger activity, or an amino acid sequence or a polynucleotide sequence modified to enhance the activity, but are not limited thereto. The replacement may specifically be performed by inserting the polynucleotide into the chromosome by homologous recombination, but is not limited thereto. The vector used herein may further include a selection marker to confirm the insertion into the chromosome. The selection marker is as described above.

The 6) introducing a foreign polynucleotide exhibiting the activity of the polypeptide may be introducing into a host cell a foreign polynucleotide encoding a polypeptide that exhibits the same/similar activity to that of the polypeptide. The foreign polynucleotide may be used without limitation regardless of its origin or sequence as long as it exhibits the same/similar activity to that of the polypeptide. The introduction may be performed by those of ordinary skill in the art by appropriately selecting a transformation method known in the art, and the expression of the introduced polynucleotide in the host cell enables to produce the polypeptide, thereby increasing its activity.

The 7) codon-optimization of the polynucleotide encoding the polypeptide may be codon-optimization of an endogenous polynucleotide to increase the transcription or translation within a host cell, or optimizing the codons thereof such that the optimized transcription and translation of the foreign polynucleotide can be achieved within the host cell.

Further, the 8) analyzing the tertiary structure of the polypeptide and thereby selecting and modifying the exposed site, or chemically modifying the same may be, for example, comparing the sequence information of the polypeptide to be analyzed with a database, in which the sequence information of known proteins is stored, to determine template protein candidates according to the degree of sequence similarity, and thus confirming the structure based on the information, thereby selecting and transforming or modifying the exposed site to be modified or chemically modified.

Such enhancement of the polypeptide activity may mean that the activity or concentration (expression level) of the corresponding polypeptide is increased relative to the activity or concentration (expression level) of the polypeptide expressed in a wild-type strain or a microorganism before modification, or that the amount of product produced from the polypeptide is increased, but is not limited thereto.

The modification of a part or all of the polynucleotide in the microorganism of the present disclosure (e.g., modification for encoding the protein variant described above) may be achieved by (a) homologous recombination using a vector for chromosomal insertion in the microorganism or genome editing using an engineered nuclease (e.g., CRISPR-Cas9), and/or (b) may be induced by light, such as ultraviolet rays and radiation, etc. and/or chemical treatments, but is not limited thereto. The method of modifying a part or all of the gene may include a method using DNA recombination technology. For example, a part or all of the gene may be deleted by injecting a nucleotide sequence or a vector containing a nucleotide sequence homologous to the target gene into the microorganism to induce homologous recombination. The injected nucleotide sequence or the vector may include a dominant selection marker, but is not limited thereto.

More specifically, the microorganism of the present disclosure may be a microorganism including a polypeptide represented by the amino acid sequence of SEQ ID NO: 26 and/or a polynucleotide represented by the nucleotide sequence of SEQ ID NO: 27; and may be a microorganism including a mutation selected from the group consisting of inactivation of a polypeptide represented by the amino acid sequence of SEQ ID NO: 16 and/or deletion of a polynucleotide represented by the nucleotide sequence of SEQ ID NO: 17.

In the microorganisms of the present disclosure, the variant, polynucleotide, etc. are as described in the other aspects above.

Even another aspect of the present disclosure provides a method for producing O-acetyl-L-homoserine or L-methionine, including: culturing a microorganism of the genus *Corynebacterium*, which includes the variant of the present disclosure or the polynucleotide of the present disclosure, in a medium.

The method for producing O-acetyl-L-homoserine or L-methionine of the present disclosure may include culturing a *Corynebacterium glutamicum* strain, which includes the variant of the present disclosure, the polynucleotide of the present disclosure, or the vector of the present disclosure, in a medium.

As used herein, the term "cultivation" means that the microorganism of the genus *Corynebacterium* of the present disclosure is grown under appropriately controlled environmental conditions. The cultivation process of the present disclosure may be performed in a suitable culture medium and culture conditions known in the art. Such a cultivation process may be easily adjusted for use by those skilled in the art according to the strain to be selected. Specifically, the cultivation may be a batch culture, a continuous culture, and/or a fed-batch culture, but is not limited thereto.

As used herein, the term "medium" refers to a mixture of materials which contains nutrient materials required for the cultivation of the microorganism of the genus *Corynebacterium* of the present disclosure as a main ingredient, and it supplies nutrient materials and growth factors, along with water that is essential for survival and growth. Specifically, the medium and other culture conditions used for culturing the microorganism of the genus *Corynebacterium* of the present disclosure may be any medium used for conventional cultivation of microorganisms without any particular limitation. However, the microorganism of the genus *Corynebacterium* of the present disclosure may be cultured under aerobic conditions in a conventional medium containing an appropriate carbon source, nitrogen source, phosphorus source, inorganic compound, amino acid, and/or vitamin, while adjusting temperature, pH, etc.

Specifically, the culture medium for the microorganism of the genus *Corynebacterium* can be found in the literature ["Manual of Methods for General Bacteriology" by the American Society for Bacteriology (Washington D.C., USA, 1981)].

In the present disclosure, the carbon source may include carbohydrates, such as glucose, saccharose, lactose, fructose, sucrose, maltose, etc.; sugar alcohols, such as mannitol, sorbitol, etc.; organic acids, such as pyruvic acid, lactic acid, citric acid, etc.; amino acids, such as glutamic acid, methionine, lysine, etc. Additionally, the carbon source may include natural organic nutrients such as starch hydrolysate, molasses, blackstrap molasses, rice bran, cassava, sugar cane molasses, and corn steep liquor, etc. Specifically, carbohydrates such as glucose and sterilized pretreated molasses (i.e., molasses converted to reducing sugar) may be used, and in addition, various other carbon sources in an appropriate amount may be used without limitation. These carbon sources may be used alone or in a combination of two or more kinds, but are not limited thereto.

The nitrogen source may include inorganic nitrogen sources, such as ammonia, ammonium sulfate, ammonium chloride, ammonium acetate, ammonium phosphate, ammonium carbonate, ammonium nitrate, etc.; amino acids, such as glutamic acid, methionine, glutamine, etc.; and organic nitrogen sources, such as peptone, NZ-amine, meat extract, yeast extract, malt extract, corn steep liquor, casein hydrolysate, fish or decomposition product thereof, defatted soybean cake or decomposition product thereof, etc. These nitrogen sources may be used alone or in a combination of two or more kinds, but are not limited thereto.

The phosphorus source may include monopotassium phosphate, dipotassium phosphate, or corresponding sodium-containing salts, etc. Examples of the inorganic compounds may include sodium chloride, calcium chloride, iron chloride, magnesium sulfate, iron sulfate, manganese sulfate, calcium carbonate, etc. Additionally, amino acids, vitamins, and/or appropriate precursors may be included. These constituting ingredients or precursors may be added to a medium in a batch or continuous manner, but these phosphorus sources are not limited thereto.

Additionally, the pH of the medium may be adjusted by adding a compound such as ammonium hydroxide, potassium hydroxide, ammonia, phosphoric acid, sulfuric acid, etc. during the cultivation of *Corynebacterium glutamicum* strain of the present disclosure in an appropriate manner. In addition, bubble formation may be prevented during the cultivation using an antifoaming agent such as fatty acid polyglycol ester. Further, oxygen gas or a gas containing oxygen may be injected to the medium order to maintain aerobic conditions of the medium; or nitrogen gas, hydrogen gas, or carbon dioxide may be injected to maintain anaerobic or microaerobic conditions, without the injection of gas, but the gas is not limited thereto.

The temperature during the cultivation of the present disclosure may be in the range from 20° C. to 45° C., specifically from 25° C. to 40° C., and the cultivation may carried be out for about 10 to 160 hours, but the cultivation is not limited thereto.

The O-acetyl-L-homoserine or L-methionine produced by the cultivation of the present disclosure may be released into the medium or remain in the cells.

The method for producing O-acetyl-L-homoserine or L-methionine of the present disclosure may further include a step of preparing the microorganism of the genus Coryne-bacterium of the present disclosure, a step of preparing a medium for culturing the microorganism, or a combination thereof (regardless of the order, in any order), for example, prior to the culturing step.

The method for producing O-acetyl-L-homoserine or L-methionine of the present disclosure may further include a step of recovering O-acetyl-L-homoserine or L-methio-nine from the culture medium (medium on which the culture was grown) or the microorganism of the genus Corynebac-terium of the present disclosure. The recovering step may be further included after the culturing step.

In the recovering step, the desired O-acetyl-L-homoserine or L-methionine may be collected using the method of culturing the microorganism of the present disclosure, for example, using a suitable method known in the art according to a batch culture, continuous culture, or fed-batch culture method. For example, methods such as centrifugation, fil-tration, treatment with a protein crystallizing precipitant (salting-out method), extraction, ultrasonic disruption, ultra-filtration, dialysis, various kinds of chromatographies such as molecular sieve chromatography (gel filtration), adsorp-tion chromatography, ion exchange chromatography, affinity chromatography, etc., HPLC or a combination thereof may be used, and the desired O-acetyl-L-homoserine or L-me-thionine can be recovered from the medium or the micro-organisms using suitable methods known in the art.

Further, the method for producing O-acetyl-L-homoserine or L-methionine of the present disclosure may further include a purification step, which may be performed using an appropriate method known in the art. In one example, when the method for producing O-acetyl-L-homoserine or L-methionine of the present disclosure includes both a recovering step and a purification step, the recovering step and the purification step may be performed continuously or intermittently regardless of the order or simultaneously, or may be integrated into one step, but the method is not limited thereto.

Moreover, the method for producing L-methionine of the present disclosure may further include a step of converting the O-acetyl-L-homoserine into L-methionine. In the method for producing L-methionine of the present disclo-sure, the conversion step may be further included after the culturing step or the recovering step. The conversion step may be performed using a suitable method known in the art (U.S. Pat. No. 8,426,171 B2). In one embodiment, the method for producing L-methionine of the present disclo-sure may include a step of producing L-methionine by contacting O-acetyl-L-homoserine and methyl mercaptan with O-acetylhomoserine sulfhydrylase, cystathionine gamma-synthase, or O-succinyl homoserine sulfhydrylase.

In the method of the present disclosure, the variant, polynucleotide, vector, microorganism, etc., are as described in the other aspects above.

Further another aspect of the present disclosure provides a composition for producing O-acetyl-L-homoserine or L-methionine, including: a microorganism of the genus Corynebacterium, which includes the variant of the present disclosure, the polynucleotide encoding the variant of the present disclosure, or the vector containing the polynucle-otide of the present disclosure; a medium on which the microorganism is grown; or a combination thereof.

The composition of the present disclosure may further include any suitable excipient commonly used in composi-tions for producing amino acids, and such excipients include, for example, preservatives, wetting agents, dispers-ing agents, suspending agents, buffers, stabilizers, or iso-tonic agents, etc., but are not limited thereto.

In the composition of the present disclosure, the variant, polynucleotide, vector, strain, medium, etc., are as described in the other aspects above.

[Mode for Carrying Out the Invention]

Hereinafter, the present disclosure will be described in detail by way of Examples. However, these Examples are merely preferred Examples given for illustrative purposes, and thus, the scope of the present disclosure is not intended to be limited to or by these Examples. Meanwhile, technical features which are not described herein can be sufficiently understood and easily carried out by those skilled in the art in the technical field of the present disclosure or in a similar technical field.

Example 1: Construction of Citrate Synthase (GltA) Variant Vector

The present inventors have discovered the 415th amino acid residue of GltA as an acetyl-CoA binding site, and predicted that when the amino acid was substituted with another amino acid, citrate synthase activity would be weak-ened as the Km value of acetyl-CoA increased. It is also known that citrate synthase activity is weakened when asparagine, which is the $241^{st}$ amino acid of GltA, is substituted with threonine (KR Patent No. 10-1915433).

Accordingly, a vector, in which lysine, which is the $415^{th}$ amino acid of GltA, is substituted with another amino acid, and asparagine, which is the $241^{st}$ amino acid, is substituted with threonine, was constructed. Specifically, a vector con-taining mutations, in which lysine, which is the $415^{th}$ amino acid of GltA, is substituted with histidine (K415H), and additionally, asparagine, which is the $241^{st}$ amino acid, is substituted with threonine (N241T), was constructed.

PCR was performed using primer pairs of SEQ ID NOS: 8 and 10, and SEQ ID NOS: 9 and 11, based on the wild-type Corynebacterium glutamicum ATCC13032 genomic DNA as a template. Overlapping PCR was performed based on the mixture of the two fragments obtained above as a template using the primer pair of SEQ ID NOS: 8 and 11 to obtain a fragment. The PCR was performed under conditions of denaturation at 94° C. for 5 minutes, followed by 30 cycles of denaturation at 94° C. for 30 seconds, annealing at 55° C. for 30 seconds, and polymerization at 72° C. for 1 minute and 30 seconds, and then polymerization at 72° C. for 5 minutes. The pDCM2 vector (SEQ ID NO: 32, Korean Application Publication No. 10-2020-0136813) was treated with SmaI, and the PCR product obtained above was sub-jected to fusion cloning. The fusion cloning was performed using an In-Fusion® HD cloning kit (Clontech). The result-ing plasmid was named pDCM2-gltA(K415H).

Additionally, a recombinant vector for introducing gltA (K415H/N241T) mutation was constructed. Specifically, the site-directed mutagenesis (BMC Biotechnology volume 9, Article number: 61 (2009)) was performed using a primer pair of SEQ ID NOS: 12 and 13, based on the pDCM2-gltA (K415H) plasmid as a template to substitute asparagine, which is the $241^{st}$ amino acid, with threonine (N241T). The thus-obtained plasmid was named pDCM2-gltA(K415H/N241T). The sequences of the primers used in this Example were shown in Table 1 below.

TABLE 1

| SEQ ID NO: | Primers | Sequences |
|---|---|---|
| 8 | Primer 1 | TCGAGCTCGGTACCC CCGTTCGTATGATCG GTTCCGCACAGGCC |
| 9 | Primer 2 | GTGCAGCAGGCAAC CAC ATCAACCGC CCACG |
| 10 | Primer 3 | CGTGGGCGGTTGAT GTG GTTGCCTGC TGCAC |
| 11 | Primer 4 | CTCTAGAGGATCCCC GCCGTAAGCAGCCTC TGGTGGAATGGTCAG C |
| 12 | Primer 5 | GCTGACCACGAGCAG ACC TGCTCCACCT CCACCGT |
| 13 | Primer 6 | ACGGTGGAGGTGGAG CAGGTCTGCTCGTGG TCAGC |

Example 2: Construction of O-Acetyl-L-Homoserine Production-Enhancing Strain and Evaluation of O-Acetyl-L-Homoserine-Producing Ability 2.1 Construction of Strain Integrated with Foreign Membrane Protein Variant YjeH In order to determine the effectiveness of the YjeH variant, which is a foreign membrane protein and an O-acetyl homoserine exporter, introduced into *Corynebacterium glutamicum* ATCC13032, a vector for chromosomal introduction containing the yjeH gene encoding the YjeH variant derived from *E. coli* (SEQ ID NO: 26) was constructed.

Specifically, in order to construct a transposase-deleted vector, a primer pair for amplifying the 5' upstream region (SEQ ID NOS: 18 and 19) and a primer pair for amplifying the 3' downstream region (SEQ ID NOS: 20 and 21) around the gene encoding the transposase (SEQ ID NO: 17, Gene No. NCgl2335) were designed. The XbaI restriction enzyme site was inserted at each end of the primers of SEQ ID NOS: 18 and 19, and the primers of SEQ ID NOS: 19 and 20 were designed so as to cross each other such that the sequence of the SmaI restriction enzyme was located at the designed site. The primer sequences are shown in Table 2.

TABLE 2

| SEQ ID NO: | Name of Sequences | Sequences |
|---|---|---|
| 18 | Tn_5 F | tgaattcgagctcggt accccCACCGACGCGCA TCTGCCT |
| 19 | Tn_5 R | GGTGTGGTGACTTTCA GCAGTTCCCGGGGGGG AGGAGGCATGTGGTGT TG |
| 20 | Tn_3 F | CAACACCACATGCCTC CTCCCCCCCGGGAACT GCTGAAAGTCACCACA CC |
| 21 | Tn_3 R | gtcgactctagaggat ccccCTCCCAAACCAT TGAGGAATGG |

PCR was performed using primer pairs of SEQ ID NOS: 18 and 19, and SEQ ID NOS: 20 and 21, based on the chromosome of the wild-type ATCC13032 as a template. The PCR was performed under conditions of denaturation at 95° C. for 5 minutes, followed by 30 cycles of denaturation at 95° C. for 30 seconds, annealing at 55° C. for 30 seconds, and polymerization at 72° C. for 30 seconds, and then polymerization at 72° C. for 7 minutes. As a result, a DNA fragment (851 bp) in the 5' upstream region and a DNA fragment (847 bp) in the 3' downstream region around the NCgl2335 gene-deleted region were obtained.

PCR was performed using a primer pair of SEQ ID NOS: 18 and 21, based on the two amplified DNA fragments as a template. The PCR was performed under conditions of denaturation at 95° C. for 5 minutes, followed by 30 cycles of denaturation at 95° C. for 30 seconds, annealing at 55° C. for 30 seconds, and polymerization at 72° C. for 90 seconds, and then polymerization at 72° C. for 7 minutes. As a result, a DNA fragment (1648 bp) including a site capable of deleting the gene encoding the transposase (SEQ ID NO: 17, Gene No. NCgl2335) was amplified.

The thus-obtained PCR products were subjected to fusion cloning into the pDCM2 vector treated with the SmaI restriction enzyme using an In-Fusion® HD cloning kit (Clontech). The cloned vector was transformed into *E. coli* DH5a, and the transformed *E. coli* was plated on a LB solid medium containing 25 mg/L of kanamycin. Colonies transformed with the plasmid into which the target gene is inserted were selected through PCR, and then the plasmid was obtained by plasmid extraction. Finally, a pDCM2-ΔNCgl2335 recombinant vector, in which the NCgl2335-deleted cassette is cloned, was constructed.

In order to determine the effectiveness of the O-acetyl homoserine exporter, a vector for chromosomal introduction containing the gene encoding the YjeH variant derived from *E. coli* (SEQ ID NO: 27) was constructed. To this end, a vector expressing the yjeH gene was constructed using the CJ7 promoter (U.S. Pat. No. 7,662,943 B2). A primer pair (SEQ ID NOS: 22 and 23) for amplifying the CJ7 promoter region and a primer pair (SEQ ID NOS: 24 and 25) for amplifying the yjeH region of *E. coli* were designed. The primer sequences are shown in Table 3 below.

TABLE 3

| SEQ ID NO: | Name of Sequences | Sequences |
|---|---|---|
| 22 | CJ7_yjeH F | ACACCACATGCC TCCTCcccAGAA ACATCCCAGCGC TAC |
| 23 | CJ7_yjeH R | AGTTCTTGTTTG AGTCCACTCATA GTGTTTCCTTTC GTTGGGT |
| 24 | yjeH F | ACCCAACGAAAG GAAACACTATGA GTGGACTCAAAC AAGAACTG |
| 25 | yjeH R | GACTTTCAGCAG TTcccgggTTAT GTGGTTATGCCA TTTTCCGG |

PCR was performed using a primer pair of SEQ ID NOS: 22 and 23, based on the pECCG117-PCJ7-gfp (U.S. Pat. No. 7,662,943 B2, p117-Pcj7-gfp) as a template, and using a primer pair of SEQ ID NOS: 24 and 25, based on the chromosome of the wild-type *E. coli* as a template. The PCR was performed under conditions of denaturation at 95° C. for 5 minutes, followed by 30 cycles of denaturation at 95° C. for 30 seconds, annealing at 55° C. for 30 seconds, and polymerization at 72° C. for 90 seconds, and then polymerization at 72° C. for 7 minutes. As a result, a DNA fragment (360 bp) of the CJ7 promoter region and a DNA fragment (1297 bp) of the yjeH gene region of *E. coli* were obtained.

PCR was performed using a primer pair of SEQ ID NOS: 22 and 24, based on the two amplified DNA fragments as a template. The PCR was performed under conditions of denaturation at 95° C. for 5 minutes, followed by 30 cycles of denaturation at 95° C. for 30 seconds, annealing at 55° C. for 30 seconds, and polymerization at 72° C. for 90 seconds, and then polymerization at 72° C. for 7 minutes. As a result, a DNA fragment (1614 bp) including the sites where the CJ7 promoter and the yjeH gene are introduced was amplified.

The gene-deleted DNA fragment obtained through PCR was cloned into the pDCM2-ΔNCgl2335 vector treated with the SmaI restriction enzyme using an In-Fusion® HD cloning kit (Clontech), and a pDCM2-ΔNCgl2335::PCJ7-yjeH (eco, WT) recombinant vector was constructed. Additionally, a recombinant vector for introducing the yjeH mutant gene (eco, F351L) was constructed.

Specifically, phenylalanine, which is the 351$^{st}$ amino acid of the YjeH amino acid sequence, was substituted with leucine (F351L) based on the pDCM2-ΔNCgl2335::PCJ7-yjeH(eco, WT) plasmid as a template using a primer pair of SEQ ID NOS: 28 and 29. The plasmid containing the thus-constructed gene encoding the YjeH(F351L) was named pDCM2-ΔNCgl2335::PCJ7-yjeH(eco,F351L). The primer sequences are shown in Table 4 below.

TABLE 4

| SEQ ID NO: | Name of Sequences | Sequences |
|---|---|---|
| 28 | F351L F | CAATGGCATCCTTATTATGATTT |
| 29 | F351L R | AAATCATAATAAGGATGCCATTG |

The thus-obtained pDCM2-ΔNCgl2335 and pDCM2-ΔNCgl2335::PCJ7-yjeH(eco,F351L) were transformed into the ATCC13032 strain by an electric-pulse method. Through a secondary cross-over, NCgl2335-deleted ATCC13032 ΔNCgl2335 and ATCC13032 ΔNCgl2335::PCJ7-yjeH(eco, F351L) were obtained on the chromosome. The insertion of the inactivated NCgl2335 gene and the yjeH gene newly introduced into *E. coli* was finally confirmed by PCR using a primer pair of SEQ ID NOS: 18 and 21, and then comparing with ATCC13032 in which the NCgl2335 gene is not inactivated.

2-2. Evaluation of O-Acetyl Homoserine-Producing Ability

In order to compare the O-acetyl homoserine (O-AH)-producing ability of the ATCC13032 ΔNCgl2335 and ATCC13032 ΔNCgl2335::PCJ7-yjeH(eco,F351L) constructed in Example 2-1, and the wild-type ATCC13032 strain, the strains were cultured in the following manner to analyze O-acetyl homoserine in the medium solution.

One platinum loop of the strains was inoculated into a 250-ml corner-baffled flask containing 25 ml of the O-acetyl homoserine production medium below, and then cultured with shaking at 200 rpm at 33° C. for 20 hours. The O-acetyl homoserine concentration was analyzed by HPLC, and the analyzed concentrations are shown in Table 5.

O-Acetyl Homoserine Production Medium (pH 7.2)

Glucose 30 g, $KH_2PO_4$ 2 g, Urea 3 g, $(NH_4)_2SO_4$ 40 g, Peptone 2.5 g, Corn Steep Liquor (CSL, Sigma) 5 g (10 ml), $MgSO_4 \cdot 7H_2O$ 0.5 g, $CaCO_3$ 20 g (based on 1 L of distilled water)

TABLE 5

| Name of Strains | O-Acetyl Homoserine (g/L) |
|---|---|
| ATCC13032 | 0.3 |
| ATCC13032 ΔNCgl2335 | 0.3 |
| ATCC13032 ΔNCgl2335 :: PCJ7-yjeH(eco, F351L) | 1.0 |

As a result, as shown in Table 5, when the control strain ATCC13032 was cultured, O-acetyl-L-homoserine was accumulated at 0.3 g/L, and it was confirmed that even when the transposase NCgl2335 gene was deleted, it had no effect on the O-acetyl-L-homoserine production. In particular, it was confirmed that when the yjeH mutant gene was expressed, the O-acetyl-L-homoserine was accumulated at 1.0 g/L.

2-3. Introduction of GltA Variants (K415H, N241T+K415H) into O-Acetyl-L-Homoserine-Producing Strains and Evaluation Thereof The O-acetyl-L-homoserine-producing ability was evaluated by introducing the GltA variants into the O-acetyl-L-homoserine-producing strains of Example 2-2. The pDCM2-gltA(K415H) and pDCM2-gltA(N241T/K415H) vectors constructed in Example 1 were transformed into each of the wild-type ATCC13032 and ATCC13032ΔNCgl2335 strains, and the O-acetyl-L-homoserine-producing strain of ATCC13032 ΔNCgl2335::PCJ7-yjeH(eco,F351L). The strains introduced with the vector on the chromosome by recombination of homologous sequences were selected in a medium containing 25 mg/L of kanamycin.

Thereafter, the gene fragments were amplified based on the *Corynebacterium glutamicum* transformants, in which the secondary recombination is completed, by PCR using a primer pair of SEQ ID NOS: 30 and 31, and the strains introduced with the gltA(K415H) and gltA(N241T/K415H) mutations were confirmed by gene sequencing analysis. The primer sequences are shown in Table 6 below.

TABLE 6

| SEQ ID NO: | Name of Sequences | Sequences |
|---|---|---|
| 30 | gltA-F | ATGTTTGAAAGGGATATCGT |
| 31 | gltA-R | TTAGCGCTCCTCGCGAGGAAC |

The recombinant strains were named based on *Corynebacterium glutamicum* as shown below, and the titer evaluation was carried in the same manner as in Example 2-2, and the results are shown in Table 7 below.

TABLE 7

| Strains | O-AH (g/L) |
|---|---|
| ATCC13032 | 0.3 |
| ATCC13032 gltA(K415H) | 0.4 |
| ATCC13032 ΔNCgl2335 | 0.3 |
| ATCC13032 ΔNCgl2335 gltA(K415H) | 0.4 |
| ATCC13032 ΔNCgl2335 gltA(K415H + N241T) | 0.5 |
| ATCC13032 ΔNCgl2335::PCJ7-yjeH(eco, F351L) | 1.0 |
| ATCC13032 ΔNCgl2335::PCJ7-yjeH(eco, F351L) gltA(K415H) | 1.3 |
| ATCC13032 ΔNCgl2335::PCJ7-yjeH(eco, F351L) gltA(K415H + N241T) | 1.5 |

As can be seen from the results above, all of the strains introduced with the GltA K415H mutation and the GltA K415H+N241T-combined mutation showed an increase in O-acetyl-L-homoserine-producing ability compared to the parent strain in which the mutations are not introduced.

The ATCC13032 ΔNCgl2335::PCJ7-yjeH(eco,F351L) gltA(K415H) was named CM04-1006 and deposited at the Korean Culture Center of Microorganisms (KCCM) under Budapest Treaty on Oct. 21, 2020, with Accession No. KCCM12809P. Additionally, the ATCC13032 ΔNCgl2335:: PCJ7-yjeH(eco,F351L) gltA(K415H+N241T) was named CM04-1007 and deposited at the Korean Culture Center of Microorganisms (KCCM) under Budapest Treaty on Oct. 21, 2020, with Accession No. KCCM12810P.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A citrate synthase variant having citrate synthase activity, wherein the amino acid at position corresponding to position 415 of the polypeptide of SEQ ID NO: 1 is histidine, the amino acid at the position corresponding to position 241 of the polypeptide of SEQ ID NO: 1 is threonine, and the variant has an amino acid sequence at least 95% identical to SEQ ID NO: 1.

2. The variant of claim 1, wherein the variant comprises the amino acid sequence of SEQ ID NO: 6.

3. The variant of claim 1, wherein the variant comprises the amino acid sequence of SEQ ID NO: 33, in which the amino acid at position 1 of SEQ ID NO: 33 is asparagine or a serine, the amino acid at position 9 of SEQ ID NO: 33 is alanine or glutamic acid, and the amino acid at position 73 of SEQ ID NO: 33 is tyrosine or cysteine.

4. The variant of claim 1, wherein the variant comprises an amino acid sequence at least 95% identical to SEQ ID NO: 6.

5. A polynucleotide encoding a citrate synthase variant having citrate synthase activity, wherein the amino acid at position corresponding to position 415 of the polypeptide of SEQ ID NO: 1 is histidine, the amino acid at the position corresponding to position 241 of the polypeptide of SEQ ID NO: 1 is threonine, and the variant has an amino acid sequence at least 95% identical to SEQ ID NO: 1.

6. A microorganism of the genus *Corynebacterium*, comprising
(a) a citrate synthase variant having citrate synthase activity, wherein the amino acid at the position corresponding to position 415 of the polypeptide of SEQ ID NO: 1 is histidine, the amino acid at the position corresponding to position 241 of the polypeptide of SEQ ID NO: 1 is threonine, and the variant has an amino acid sequence at least 95% identical to SEQ ID NO: 1; or
(b) a polynucleotide encoding the citrate synthase variant of (a).

7. The microorganism of claim 6, wherein the microorganism has an O-acetyl-L-homoserine-producing ability.

8. The microorganism of claim 6, wherein the microorganism is *Corynebacterium glutamicum*.

9. A method for producing O-acetyl-L-homoserine or L-methionine, comprising culturing the microorganism of claim 6 in a medium.

10. The method of claim 9, wherein the method further comprises recovering O-acetyl-L-homoserine or L-methionine from the cultured medium or microorganism.

11. The method of claim 9, wherein the method for producing L-methionine further comprises converting the O-acetyl-L-homoserine into L-methionine.

12. A composition for producing O-acetyl-L-homoserine or L-methionine, that comprises the microorganism of claim 6 and a growth medium.

13. The variant of claim 1, wherein the variant comprises an amino acid sequence at least 98% identical to SEQ ID NO: 1.

14. The variant of claim 1, wherein the variant comprises an amino acid sequence at least 99% identical to SEQ ID NO: 1.

15. A microorganism comprising the variant of claim 1.

16. A microorganism comprising the variant of claim 5.

17. A method for producing O-acetyl-L-homoserine or L-methionine, comprising culturing the microorganism of claim 16 in a medium.

18. The method of claim 17, wherein the method further comprises recovering O-acetyl-L-homoserine or L-methionine from the cultured medium or microorganism.

19. A method for producing O-acetyl-L-homoserine or L-methionine, comprising culturing the microorganism of claim 15 in a medium.

20. The method of claim 19, wherein the method further comprises recovering O-acetyl-L-homoserine or L-methionine from the cultured medium or microorganism.

* * * * *

SEQUENCE LISTING

<160> NUMBER OF SEQ ID NOS: 33

<210> SEQ ID NO 1
<211> LENGTH: 437
<212> TYPE: PRT
<213> ORGANISM: Unknown
<220> FEATURE:
<223> OTHER INFORMATION: ATCC 13032 GltA AA

<400> SEQUENCE: 1

```
Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175
```

Val Pro Met Leu Ala Ala Tyr Ala His Arg Ala Arg Lys Gly Ala Pro
                180                185                190

Tyr Met Tyr Pro Asp Asn Ser Leu Asn Ala Arg Glu Asn Phe Leu Arg
                195                200                205

Met Met Phe Gly Tyr Pro Thr Glu Pro Tyr Glu Ile Asp Pro Ile Met
        210                215                220

Val Lys Ala Leu Asp Lys Leu Leu Ile Leu His Ala Asp His Glu Gln
225                230                235                240

Asn Cys Ser Thr Ser Thr Val Arg Met Ile Gly Ser Ala Gln Ala Asn
                245                250                255

Met Phe Val Ser Ile Ala Gly Gly Ile Asn Ala Leu Ser Gly Pro Leu
                260                265                270

His Gly Gly Ala Asn Gln Ala Val Leu Glu Met Leu Glu Asp Ile Lys
        275                280                285

Ser Asn His Gly Gly Asp Ala Thr Glu Phe Met Asn Lys Val Lys Asn
        290                295                300

Lys Glu Asp Gly Val Arg Leu Met Gly Phe Gly His Arg Val Tyr Lys
305                310                315                320

Asn Tyr Asp Pro Arg Ala Ala Ile Val Lys Glu Thr Ala His Glu Ile
                325                330                335

Leu Glu His Leu Gly Gly Asp Asp Leu Leu Asp Leu Ala Ile Lys Leu
                340                345                350

Glu Glu Ile Ala Leu Ala Asp Asp Tyr Phe Ile Ser Arg Lys Leu Tyr
        355                360                365

Pro Asn Val Asp Phe Tyr Thr Gly Leu Ile Tyr Arg Ala Met Gly Phe
        370                375                380

Pro Thr Asp Phe Phe Thr Val Leu Phe Ala Ile Gly Arg Leu Pro Gly
385                390                395                400

Trp Ile Ala His Tyr Arg Glu Gln Leu Gly Ala Ala Gly Asn Lys Ile
                405                410                415

Asn Arg Pro Arg Gln Val Tyr Thr Gly Asn Glu Ser Arg Lys Leu Val
                420                425                430

Pro Arg Glu Glu Arg
        435

<210> SEQ ID NO 2
<211> LENGTH: 1314
<212> TYPE: DNA
<213> ORGANISM: Unknown
<220> FEATURE:
<223> OTHER INFORMATION: ATCC13032 GltA NT

<400> SEQUENCE: 2
atgtttgaaa gggatatcgt ggctactgat aacaacaagg ctgtcctgca ctaccccggt          60
ggcgagttcg aaatggacat catcgaggct tctgagggta acaacggtgt tgtcctgggc         120
aagatgctgt ctgagactgg actgatcact tttgacccag ttatgtgag cactggctcc         180 accgagtcga agatcaccta catcgatggc gatgcgggaa tcctgcgtta ccgcggctat         240
gacatcgctg atctggctga gaatgccacc ttcaacgagg tttcttacct acttatcaac         300
ggtgagctac caaccccaga tgagcttcac aagtttaacg acgagattcg ccaccacacc         360
cttctggacg aggacttcaa gtcccagttc aacgtgttcc cacgcgacgc tcacccaatg         420
gcaaccttgg cttcctcggt taacattttg tctacctact accaggacca gctgaaccca         480
ctcgatgagg cacagcttga taaggcaacc gttcgcctca tggcaaaggt tccaatgctg         540

```
gctgcgtacg cacaccgcgc acgcaagggt gctccttaca tgtacccaga caactccctc     600
aatgcgcgtg agaacttcct gcgcatgatg ttcggttacc caaccgagcc atacgagatc     660
gacccaatca tggtcaaggc tctggacaag ctgctcatcc tgcacgctga ccacgagcag     720
aactgctcca cctccaccgt tcgtatgatc ggttccgcac aggccaacat gtttgtctcc     780
atcgctggtg gcatcaacgc tctgtccggc ccactgcacg gtggcgcaaa ccaggctgtt     840
ctggagatgc tcgaagacat caagagcaac cacggtggcg acgcaaccga gttcatgaac     900
aaggtcaaga acaaggaaga cggcgtccgc ctcatgggct tcggacaccg cgtttacaag     960
aactacgatc cacgtgcagc aatcgtcaag gagaccgcac acgagatcct cgagcacctc    1020
ggtggcgacg atcttctgga tctggcaatc aagctggaag aaattgcact ggctgatgat    1080
tacttcatct cccgcaagct ctacccgaac gtagacttct acaccggcct gatctaccgc    1140
gcaatgggct tcccaactga cttcttcacc gtattgttcg caatcggtcg tctgccagga    1200
tggatcgctc actaccgcga gcagctcggt gcagcaggca acaagatcaa ccgcccacgc    1260
caggtctaca ccggcaacga atcccgcaag ttggttcctc gcgaggagcg ctaa          1314
```

```
<210> SEQ ID NO 3
<211> LENGTH: 54
<212> TYPE: PRT
<213> ORGANISM: Unknown
<220> FEATURE:
<223> OTHER INFORMATION: ATCC 13032 GltA K415H 362~415

<400> SEQUENCE: 3

Phe Ile Ser Arg Lys Leu Tyr Pro Asn Val Asp Phe Tyr Thr Gly Leu
1               5                   10                  15

Ile Tyr Arg Ala Met Gly Phe Pro Thr Asp Phe Phe Thr Val Leu Phe
            20                  25                  30

Ala Ile Gly Arg Leu Pro Gly Trp Ile Ala His Tyr Arg Glu Gln Leu
        35                  40                  45

Gly Ala Ala Gly Asn His
    50
```

```
<210> SEQ ID NO 4
<211> LENGTH: 437
<212> TYPE: PRT
<213> ORGANISM: Artificial Sequence
<220> FEATURE:
<223> OTHER INFORMATION: ATCC13032 GltA K415H AA

<400> SEQUENCE: 4

Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110
```

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
                180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
        210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
                260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
                340                 345                 350

Glu Glu Ile Ala Leu Ala Asp Asp Tyr Phe Ile Ser Arg Lys Leu Tyr
        355                 360                 365

Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn His Ile
                405                 410                 415

Asn Arg Pro Arg Gln Val Tyr Thr Gly Asn Glu Ser Arg Lys Leu Val
                420                 425                 430

Pro Arg Glu Glu Arg
        435

<210> SEQ ID NO 5
<211> LENGTH: 1314
<212> TYPE: DNA
<213> ORGANISM: Artificial Sequence
<220> FEATURE:
<223> OTHER INFORMATION: ATCC13032 GltA K415H NT

<400> SEQUENCE: 5
atgtttgaaa gggatatcgt ggctactgat aacaacaagg ctgtcctgca ctaccccggt      60
ggcgagttcg aaatggacat catcgaggct tctgagggta caacggtgt tgtcctgggc      120 aagatgctgt ctgagactgg actgatcact tttgacccag ttatgtgag cactggctcc      180

-continued

```
accgagtcga agatcaccta catcgatggc gatgcgggaa tcctgcgtta ccgcggctat      240
gacatcgctg atctggctga gaatgccacc ttcaacgagg tttcttacct acttatcaac      300
ggtgagctac caaccccaga tgagcttcac aagtttaacg acgagattcg ccaccacacc      360
cttctggacg aggacttcaa gtcccagttc aacgtgttcc cacgcgacgc tcacccaatg      420
gcaaccttgg cttcctcggt taacattttg tctacctact accaggacca gctgaaccca      480
ctcgatgagc cacagcttga taaggcaacc gttcgcctca tggcaaaggt tccaatgctg      540
gctgcgtacg cacaccgcgc acgcaagggt gctccttaca tgtacccaga caactccctc      600
aatgcgcgtg agaacttcct cgcgcatgatg ttcggttacc caaccgagcc atacgagatc      660
gacccaatca tggtcaaggc tctggacaag ctgctcatcc tgcacgctga ccacgagcag      720
aactgctcca cctccaccgt tcgtatgatc ggttccgcac aggccaacat gtttgtctcc      780
atcgctggtg gcatcaacgc tctgtccggc ccactgcacg gtggcgcaaa ccaggctgtt      840
ctggagatgc tcgaagacat caagagcaac cacggtggcg acgcaaccga gttcatgaac      900
aaggtcaaga acaaggaaga cggcgtccgc ctcatgggct tcggacaccg cgtttacaag      960
aactacgatc cacgtgcagc aatcgtcaag agagaccgcac acgagatcct cgagcacctc     1020
ggtggcgacg atcttctgga tctggcaatc aagctggaag aaattgcact ggctgatgat     1080
tacttcatct cccgcaagct ctacccgaac gtagacttct acaccggcct gatctaccgc     1140
gcaatgggct tcccaactga cttcttcacc gtattgttcg caatcggtcg tctgccagga     1200
tggatcgctc actaccgcga gcagctcggt gcagcaggca accacatcaa ccgcccacgc     1260
caggtctaca ccggcaacga atcccgcaag ttggttcctc gcgaggagcg ctaa           1314
```

```
<210> SEQ ID NO 6
<211> LENGTH: 437
<212> TYPE: PRT
<213> ORGANISM: Artificial Sequence
<220> FEATURE:
<223> OTHER INFORMATION: ATCC13032 GltA K415H+ N241T AA

<400> SEQUENCE: 6

Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160
```

```
Leu Asp Glu Ala Gln Leu Asp Lys Ala Thr Val Arg Leu Met Ala Lys
            165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
            195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240

Thr Cys Ser Thr Ser Thr Val Arg Met Ile Gly Ser Ala Gln Ala Asn
            245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
            275                 280                 285

Ser Asn His Gly Gly Asp Ala Thr Glu Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
            325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
            355                 360                 365

Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn His Ile
            405                 410                 415

Asn Arg Pro Arg Gln Val Tyr Thr Gly Asn Glu Ser Arg Lys Leu Val
            420                 425                 430

Pro Arg Glu Glu Arg
            435

<210> SEQ ID NO 7
<211> LENGTH: 1314
<212> TYPE: DNA
<213> ORGANISM: Artificial Sequence
<220> FEATURE:
<223> OTHER INFORMATION: ATCC13032 GltA K415H+ N241T NT

<400> SEQUENCE: 7
atgtttgaaa gggatatcgt ggctactgat aacaacaagg ctgtcctgca ctaccccggt     60
ggcgagttcg aaatggacat catcgaggct tctgagggta acaacggtgt tgtcctgggc    120
aagatgctgt ctgagactgg actgatcact tttgacccag ttatgtgag cactggctcc    180 accgagtcga agatcaccta catcgatggc gatgcgggaa tcctgcgtta ccgcggctat    240
gacatcgctg atctggctga gaatgccacc ttcaacgagg tttcttacct acttatcaac    300
ggtgagctac caaccccaga tgagcttcac aagtttaacg acgagattcg ccaccacacc    360
cttctggacg aggacttcaa gtcccagttc aacgtgttcc cacgcgacgc tcacccaatg    420
gcaaccttgg cttcctcggt taacattttg tctacctact accaggacca gctgaaccca    480
```

-continued

```
ctcgatgagg cacagcttga taaggcaacc gttcgcctca tggcaaaggt tccaatgctg     540
gctgcgtacg cacaccgcgc acgcaagggt gctccttaca tgtacccaga caactccctc     600
aatgcgcgtg agaacttcct gcgcatgatg ttcggttacc caaccgagcc atacgagatc     660
gacccaatca tggtcaaggc tctggacaag ctgctcatcc tgcacgctga ccacgagcag     720
acctgctcca cctccaccgt tcgtatgatc ggttccgcac aggccaacat gtttgtctcc     780
atcgctggtg gcatcaacgc tctgtccggc ccactgcacg gtggcgcaaa ccaggctgtt     840
ctggagatgc tcgaagacat caagagcaac cacggtggcg acgcaaccga gttcatgaac     900
aaggtcaaga acaaggaaga cggcgtccgc ctcatgggct tcggacaccg cgtttacaag     960
aactacgatc cacgtgcagc aatcgtcaag gagaccgcac acgagatcct cgagcacctc    1020
ggtggcgacg atcttctgga tctggcaatc aagctggaag aaattgcact ggctgatgat    1080
tacttcatct cccgcaagct ctacccgaac gtagacttct acaccggcct gatctaccgc    1140
gcaatgggct tcccaactga cttcttcacc gtattgttcg caatcggtcg tctgccagga    1200
tggatcgctc actaccgcga gcagctcggt gcagcaggca accacatcaa ccgcccacgc    1260
caggtctaca ccggcaacga atcccgcaag ttggttcctc gcgaggagcg ctaa          1314
```

```
<210> SEQ ID NO 8
<211> LENGTH: 44
<212> TYPE: DNA
<213> ORGANISM: Artificial Sequence
<220> FEATURE:
<223> OTHER INFORMATION: primer 1

<400> SEQUENCE: 8
tcgagctcgg tacccccgtt cgtatgatcg gttccgcaca ggcc                      44

<210> SEQ ID NO 9
<211> LENGTH: 31
<212> TYPE: DNA
<213> ORGANISM: Artificial Sequence
<220> FEATURE:
<223> OTHER INFORMATION: primer 2

<400> SEQUENCE: 9
gtgcagcagg caaccacatc aaccgcccac g                                    31

<210> SEQ ID NO 10
<211> LENGTH: 31
<212> TYPE: DNA
<213> ORGANISM: Artificial Sequence
<220> FEATURE:
<223> OTHER INFORMATION: primer 3

<400> SEQUENCE: 10
cgtgggcggt tgatgtggtt gcctgctgca c                                    31

<210> SEQ ID NO 11
<211> LENGTH: 46
<212> TYPE: DNA
<213> ORGANISM: Artificial Sequence
<220> FEATURE:
<223> OTHER INFORMATION: primer 4

<400> SEQUENCE: 11
ctctagagga tccccgccgt aagcagcctc tggtggaatg gtcagc                    46

<210> SEQ ID NO 12
```

-continued

<211> LENGTH: 35
<212> TYPE: DNA
<213> ORGANISM: Artificial Sequence
<220> FEATURE:
<223> OTHER INFORMATION: primer 5

<400> SEQUENCE: 12
gctgaccacg agcagacctg ctccacctcc accgt                                    35

<210> SEQ ID NO 13
<211> LENGTH: 35
<212> TYPE: DNA
<213> ORGANISM: Artificial Sequence
<220> FEATURE:
<223> OTHER INFORMATION: primer 6

<400> SEQUENCE: 13
acggtggagg tggagcaggt ctgctcgtgg tcagc                                    35

<210> SEQ ID NO 14
<211> LENGTH: 418
<212> TYPE: PRT
<213> ORGANISM: Unknown
<220> FEATURE:
<223> OTHER INFORMATION: YjeH AA

<400> SEQUENCE: 14

Met Ser Gly Leu Lys Gln Glu Leu Gly Leu Ala Gln Gly Ile Gly Leu
1               5                   10                  15

Leu Ser Thr Ser Leu Leu Gly Thr Gly Val Phe Ala Val Pro Ala Leu
            20                  25                  30

Ala Ala Leu Val Ala Gly Asn Asn Ser Leu Trp Ala Trp Pro Val Leu
        35                  40                  45

Ile Ile Leu Val Phe Pro Ile Ala Ile Val Phe Ala Ile Leu Gly Arg
    50                  55                  60

His Tyr Pro Ser Ala Gly Gly Val Ala His Phe Val Gly Met Ala Phe
65                  70                  75                  80

Gly Ser Arg Leu Glu Arg Val Thr Gly Trp Leu Phe Leu Ser Val Ile
                85                  90                  95

Pro Val Gly Leu Pro Ala Ala Leu Gln Ile Ala Ala Gly Phe Gly Gln
            100                 105                 110

Ala Met Phe Gly Trp His Ser Trp Gln Leu Leu Leu Ala Glu Leu Gly
        115                 120                 125

Thr Leu Ala Leu Val Trp Tyr Ile Gly Thr Arg Gly Ala Ser Ser Ser
    130                 135                 140

Ala Asn Leu Gln Thr Val Ile Ala Gly Leu Ile Val Ala Leu Ile Val
145                 150                 155                 160

Ala Ile Trp Trp Ala Gly Asp Ile Lys Pro Ala Asn Ile Pro Phe Pro
                165                 170                 175

Ala Pro Gly Asn Ile Glu Leu Thr Gly Leu Phe Ala Ala Leu Ser Val
            180                 185                 190

Met Phe Trp Cys Phe Val Gly Leu Glu Ala Phe Ala His Leu Ala Ser
        195                 200                 205

Glu Phe Lys Asn Pro Glu Arg Asp Phe Pro Arg Ala Leu Met Ile Gly
    210                 215                 220

Leu Leu Leu Ala Gly Leu Val Tyr Trp Gly Cys Thr Val Val Val Leu
225                 230                 235                 240

His Phe Asp Ala Tyr Gly Glu Lys Met Ala Ala Ala Ser Leu Pro
                245                 250                 255

-continued

```
Lys Ile Val Val Gln Leu Phe Gly Val Gly Ala Leu Trp Ile Ala Cys
        260                 265                 270

Val Ile Gly Tyr Leu Ala Cys Phe Ala Ser Leu Asn Ile Tyr Ile Gln
        275                 280                 285

Ser Phe Ala Arg Leu Val Trp Ser Gln Ala Gln His Asn Pro Asp His
        290                 295                 300

Tyr Leu Ala Arg Leu Ser Ser Arg His Ile Pro Asn Asn Ala Leu Asn
305                 310                 315                 320

Ala Val Leu Gly Cys Cys Val Val Ser Thr Leu Val Ile His Ala Leu
                325                 330                 335

Glu Ile Asn Leu Asp Ala Leu Ile Ile Tyr Ala Asn Gly Ile Phe Ile
        340                 345                 350

Met Ile Tyr Leu Leu Cys Met Leu Ala Gly Cys Lys Leu Leu Gln Gly
        355                 360                 365

Arg Tyr Arg Leu Leu Ala Val Val Gly Gly Leu Leu Cys Val Leu Leu
        370                 375                 380

Leu Ala Met Val Gly Trp Lys Ser Leu Tyr Ala Leu Ile Met Leu Ala
385                 390                 395                 400

Gly Leu Trp Leu Leu Leu Pro Lys Arg Lys Thr Pro Glu Asn Gly Ile
                405                 410                 415

Thr Thr

<210> SEQ ID NO 15
<211> LENGTH: 1257
<212> TYPE: DNA
<213> ORGANISM: Unknown
<220> FEATURE:
<223> OTHER INFORMATION: YjeH NT

<400> SEQUENCE: 15
atgagtggac tcaaacaaga actggggctg gcccagggca ttggcctgct atcgacgtca    60
ttattaggca ctggcgtgtt tgccgttcct gcgttagctg cgctggtagc gggcaataac   120
agcctgtggg cgtggcccgt tttgattatc ttagtgttcc cgattgcgat tgtgtttgcg   180
attctgggtc gccactatcc cagcgcaggc ggcgtcgcgc acttcgtcgg tatggcgttt   240
ggttcgcggc ttgagcgagt caccggctgg ctgtttttat cggtcattcc cgtgggtttg   300
cctgccgcac tacaaattgc cgccgggttc ggccaggcga tgtttggctg gcatagctgg   360
caactgttgt tggcagaact cggtacgctg gcgctggtgt ggtatatcgg tactcgcggt   420
gccagttcca gtgctaatct acaaaccgtt attgccggac ttatcgtcgc gctgattgtc   480
gctatctggt gggcgggcga tatcaaacct gcgaatatcc cctttccggc acctggtaat   540
atcgaactta ccgggttatt tgctgcgtta tcagtgatgt ctggtgtttt tgtcggtctg   600
gaggcatttg cccatctcgc ctcggaattt aaaaatccag agcgtgattt cctcgtgct    660 ttgatgattg tctgctgct ggcaggatta gtctactggg gctgtacggt agtcgtctta   720
cacttcgacg cctatggtga aaaaatggcg gcggcagcat cgcttccaaa aattgtagtg   780
cagttgttcg gtgtaggagc gttatggatt gcctgcgtga ttggctatct ggcctgcttt   840
gccagtctca acatttatat acagagcttc gcccgcctgg tctggtcgca ggcgcaacat   900
aatcctgacc actacctggc acgcctctct tctcgccata tcccgaataa tgccctcaat   960
gcggtgctcg gctgctgtgt ggtgagcact ttggtgattc atgctttaga gatcaatctc  1020
gacgctctta ttatttatgc caatggcatc tttattatga tttatctgtt atgcatgctg  1080
```

-continued

```
gcaggctgta aattattgca aggacgttat cgactactgg cggtggttgg cgggctgtta     1140
tgcgttctgt tactggcaat ggtcggctgg aaaagtctct atgcgctgat catgctggcg     1200
gggttatggc tgttgctgcc aaaacgaaaa acgccggaaa atggcataac cacataa       1257
```

```
<210> SEQ ID NO 16
<211> LENGTH: 88
<212> TYPE: PRT
<213> ORGANISM: Unknown
<220> FEATURE:
<223> OTHER INFORMATION: NCgl2335 AA

<400> SEQUENCE: 16

Met Ala Tyr Thr Phe Asp His Val Val Ala Trp Arg Trp Cys Thr Lys
1               5                   10                  15

Glu Asp Ala Tyr Asn Tyr Thr His Leu Phe Asp Gln Leu Gln Pro Pro
            20                  25                  30

Leu Ile Val Thr Thr Asp Gly Gln Lys Arg Arg Thr Gln Ser His His
        35                  40                  45

His Asp Leu Ala Asp Asn Glu Asn Pro Thr Leu Pro Arg Pro Arg Gln
    50                  55                  60

Thr Gln Arg Pro Lys Thr Arg His Pro Lys Thr Arg Ala Glu Leu Ala
65                  70                  75                  80

Glu Lys His Ser Gly Val Ser Pro
                85
```

```
<210> SEQ ID NO 17
<211> LENGTH: 267
<212> TYPE: DNA
<213> ORGANISM: Unknown
<220> FEATURE:
<223> OTHER INFORMATION: NCgl2335 NT

<400> SEQUENCE: 17
gtggcctaca ccttcgacca cgtcgtcgcc tggcgctggt gcaccaaaga agacgcctac       60
aactacaccc acctcttcga tcaactccaa ccacccttaa tcgtgaccac cgacggacaa      120
aaaaggcgca ctcaaagcca tcaccacgac ctggccgaca cgaaaatcc aacgctgcct       180 cgtccacgtc aaacgcaacg tccaaaaaca cgtcaccota agaccgtgc tgagctcgcc       240 gaaaagcact ccggggtctc tccttga                                          267
```

```
<210> SEQ ID NO 18
<211> LENGTH: 39
<212> TYPE: DNA
<213> ORGANISM: Artificial Sequence
<220> FEATURE:
<223> OTHER INFORMATION: Tn_5 F

<400> SEQUENCE: 18
tgaattcgag ctcggtaccc caccgacgcg catctgcct                             39
```

```
<210> SEQ ID NO 19
<211> LENGTH: 50
<212> TYPE: DNA
<213> ORGANISM: Artificial Sequence
<220> FEATURE:
<223> OTHER INFORMATION: Tn_5 R

<400> SEQUENCE: 19
ggtgtggtga ctttcagcag ttcccggggg ggaggaggca tgtggtgttg                 50
```

-continued

<210> SEQ ID NO 20
<211> LENGTH: 50
<212> TYPE: DNA
<213> ORGANISM: Artificial Sequence
<220> FEATURE:
<223> OTHER INFORMATION: Tn_3 F

<400> SEQUENCE: 20
caacaccaca tgcctcctcc cccccgggaa ctgctgaaag tcaccacacc                    50

<210> SEQ ID NO 21
<211> LENGTH: 42
<212> TYPE: DNA
<213> ORGANISM: Artificial Sequence
<220> FEATURE:
<223> OTHER INFORMATION: Tn_3 R

<400> SEQUENCE: 21
gtcgactcta gaggatcccc ctcccaaacc attgaggaat gg                           42

<210> SEQ ID NO 22
<211> LENGTH: 39
<212> TYPE: DNA
<213> ORGANISM: Artificial Sequence
<220> FEATURE:
<223> OTHER INFORMATION: CJ7_yjeH F

<400> SEQUENCE: 22
acaccacatg cctcctcccc agaaacatcc cagcgctac                               39

<210> SEQ ID NO 23
<211> LENGTH: 43
<212> TYPE: DNA
<213> ORGANISM: Artificial Sequence
<220> FEATURE:
<223> OTHER INFORMATION: CJ7_yjeH R

<400> SEQUENCE: 23
agttcttgtt tgagtccact catagtgttt cctttcgttg ggt                         43

<210> SEQ ID NO 24
<211> LENGTH: 44
<212> TYPE: DNA
<213> ORGANISM: Artificial Sequence
<220> FEATURE:
<223> OTHER INFORMATION: yjeH F

<400> SEQUENCE: 24
acccaacgaa aggaaacact atgagtggac tcaaacaaga actg                         44

<210> SEQ ID NO 25
<211> LENGTH: 44
<212> TYPE: DNA
<213> ORGANISM: Artificial Sequence
<220> FEATURE:
<223> OTHER INFORMATION: yjeH R

<400> SEQUENCE: 25
gactttcagc agttcccggg ttatgtggtt atgccatttt ccgg                        44

<210> SEQ ID NO 26
<211> LENGTH: 418
<212> TYPE: PRT
<213> ORGANISM: Artificial Sequence
<220> FEATURE:
<223> OTHER INFORMATION: yjeH F351L AA

<400> SEQUENCE: 26

Met Ser Gly Leu Lys Gln Glu Leu Gly Leu Ala Gln Gly Ile Gly Leu
1               5                   10                  15

Leu Ser Thr Ser Leu Leu Gly Thr Gly Val Phe Ala Val Pro Ala Leu
                20                  25                  30

Ala Ala Leu Val Ala Gly Asn Asn Ser Leu Trp Ala Trp Pro Val Leu
            35                  40                  45

Ile Ile Leu Val Phe Pro Ile Ala Ile Val Phe Ala Ile Leu Gly Arg
        50                  55                  60

His Tyr Pro Ser Ala Gly Gly Val Ala His Phe Val Gly Met Ala Phe
65                  70                  75                  80

Gly Ser Arg Leu Glu Arg Val Thr Gly Trp Leu Phe Leu Ser Val Ile
                85                  90                  95

Pro Val Gly Leu Pro Ala Ala Leu Gln Ile Ala Ala Gly Phe Gly Gln
                100                 105                 110

Ala Met Phe Gly Trp His Ser Trp Gln Leu Leu Leu Ala Glu Leu Gly
            115                 120                 125

Thr Leu Ala Leu Val Trp Tyr Ile Gly Thr Arg Gly Ala Ser Ser Ser
        130                 135                 140

Ala Asn Leu Gln Thr Val Ile Ala Gly Leu Ile Val Ala Leu Ile Val
145                 150                 155                 160

Ala Ile Trp Trp Ala Gly Asp Ile Lys Pro Ala Asn Ile Pro Phe Pro
                165                 170                 175

Ala Pro Gly Asn Ile Glu Leu Thr Gly Leu Phe Ala Ala Leu Ser Val
            180                 185                 190

Met Phe Trp Cys Phe Val Gly Leu Glu Ala Phe Ala His Leu Ala Ser
            195                 200                 205

Glu Phe Lys Asn Pro Glu Arg Asp Phe Pro Arg Ala Leu Met Ile Gly
        210                 215                 220

Leu Leu Leu Ala Gly Leu Val Tyr Trp Gly Cys Thr Val Val Val Leu
225                 230                 235                 240

His Phe Asp Ala Tyr Gly Glu Lys Met Ala Ala Ala Ser Leu Pro
            245                 250                 255

Lys Ile Val Val Gln Leu Phe Gly Val Gly Ala Leu Trp Ile Ala Cys
            260                 265                 270

Val Ile Gly Tyr Leu Ala Cys Phe Ala Ser Leu Asn Ile Tyr Ile Gln
        275                 280                 285

Ser Phe Ala Arg Leu Val Trp Ser Gln Ala Gln His Asn Pro Asp His
    290                 295                 300

Tyr Leu Ala Arg Leu Ser Ser Arg His Ile Pro Asn Asn Ala Leu Asn
305                 310                 315                 320

Ala Val Leu Gly Cys Cys Val Val Ser Thr Leu Val Ile His Ala Leu
            325                 330                 335

Glu Ile Asn Leu Asp Ala Leu Ile Ile Tyr Ala Asn Gly Ile Leu Ile
        340                 345                 350

Met Ile Tyr Leu Leu Cys Met Leu Ala Gly Cys Lys Leu Leu Gln Gly
        355                 360                 365

Arg Tyr Arg Leu Leu Ala Val Val Gly Gly Leu Leu Cys Val Leu Leu
    370                 375                 380

Leu Ala Met Val Gly Trp Lys Ser Leu Tyr Ala Leu Ile Met Leu Ala
385                 390                 395                 400

Gly Leu Trp Leu Leu Leu Pro Lys Arg Lys Thr Pro Glu Asn Gly Ile
                405                 410                 415

Thr Thr

<210> SEQ ID NO 27
<211> LENGTH: 1257
<212> TYPE: DNA
<213> ORGANISM: Artificial Sequence
<220> FEATURE:
<223> OTHER INFORMATION: yjeH F351L NT

<400> SEQUENCE: 27
atgagtggac tcaaacaaga actggggctg gcccagggca ttggcctgct atcgacgtca        60
ttattaggca ctggcgtgtt tgccgttcct gcgttagctg cgctggtagc gggcaataac       120
agcctgtggg cgtggcccgt tttgattatc ttagtgttcc cgattgcgat tgtgtttgcg       180
attctgggtc gccactatcc cagcgcaggc ggcgtcgcgc acttcgtcgg tatggcgttt       240
ggttcgcggc ttgagcgagt caccggctgg ctgaatttat cggtcattcc cgtgggtttg       300
cctgccgcac tacaaattgc cgccgggttc ggccaggcga tgtttggctg gcatagctgg       360
caactgttgt tggcagaact cggtacgctg gcgctggtgt ggtatatcgg tactcgcggt       420
gccagttcca gtgctaatct acaaaccgtt attgccggac ttatcgtcgc gctgattgtc       480
gctatctggt gggcgggcga tatcaaacct gcgaatatcc cctttccggc acctggtaat       540
atcgaactta ccgggttatt tgctgcgtta tcagtgatgt tctggtgttt tgtcggtctg       600
gaggcatttg cccatctcgc ctcggaattt aaaaatccag agcgtgattt tcctcgtgct       660
ttgatgattg gtctgctgct ggcaggatta gtctactggg gctgtacggt agtcgtctta       720
cacttcgacg cctatggtga aaaaatggcg gcggcagcat cgcttccaaa aattgtagtg       780
cagttgttcg gtgtaggagc gttatggatt gcctgcgtga ttggctatct ggcctgcttt       840
gccagtctca acatttatat acagagcttc gcccgcctgg tctggtcgca ggcgcaacat       900
aatcctgacc actacctggc acgcctctct tctcgccata tcccgaataa tgccctcaat       960
gcggtgctcg gctgctgtgt ggtgagcact ttggtgattc atgctttaga gatcaatctg      1020
gacgctctta ttatttatgc caatggcatc cttattatga tttatctgtt atgcatgctg      1080
gcaggctgta aattattgca aggacgttat cgactactgg cggtggttgg cgggctgtta      1140
tgcgttctgt tactggcaat ggtcggctgg aaaagtctct atgcgctgat catgctggcg      1200
gggttatggc tgttgctgcc aaaacgaaaa acgccggaaa tggcataac acataa          1257

<210> SEQ ID NO 28
<211> LENGTH: 23
<212> TYPE: DNA
<213> ORGANISM: Artificial Sequence
<220> FEATURE:
<223> OTHER INFORMATION: F351L F

<400> SEQUENCE: 28
caatggcatc cttattatga ttt                                                23

<210> SEQ ID NO 29
<211> LENGTH: 23
<212> TYPE: DNA
<213> ORGANISM: Artificial Sequence
<220> FEATURE:
<223> OTHER INFORMATION: F351L R

<400> SEQUENCE: 29
aaatcataat aaggatgcca ttg                                                23

```
<210> SEQ ID NO 30
<211> LENGTH: 20
<212> TYPE: DNA
<213> ORGANISM: Artificial Sequence
<220> FEATURE:
<223> OTHER INFORMATION: gltA-F

<400> SEQUENCE: 30
atgtttgaaa gggatatcgt                                                    20

<210> SEQ ID NO 31
<211> LENGTH: 21
<212> TYPE: DNA
<213> ORGANISM: Artificial Sequence
<220> FEATURE:
<223> OTHER INFORMATION: gltA-R

<400> SEQUENCE: 31
ttagcgctcc tcgcgaggaa c                                                  21

<210> SEQ ID NO 32
<211> LENGTH: 5803
<212> TYPE: DNA
<213> ORGANISM: Artificial Sequence
<220> FEATURE:
<223> OTHER INFORMATION: pDCM2
<220> FEATURE:
<221> NAME/KEY: misc_feature
<222> LOCATION: (2895)..(2895)
<223> OTHER INFORMATION: n is a, c, g, or t

<400> SEQUENCE: 32
gttcgcttgc tgtccataaa accgcccagt ctagctatcg ccatgtaagc ccactgcaag       60
ctacctgctt tctctttgcg cttgcgtttt cccttgtcca gatagcccag tagctgacat      120
tcatccgggg tcagcaccgt ttctgcggac tggctttcta cgtgttccgc ttcctttagc      180
agcccttgcg ccctgagtgc ttgcggcagc gtgaagctag cttttatcgc cattcgccat      240
tcaggctgcg caactgttgg aagggcgat cggtgcgggc ctcttcgcta ttacgccagc       300
tggcgaaagg gggatgtgct gcaaggcgat taagttgggt aacgccaggg ttttcccagt      360
cacgacgttg taaaacgacg gccagtgaat tcgagctcgg tacccgggga tcctctagag      420
tcgacctgca ggcatgcaag cttggcgtaa tcatggtcat agctgtttcc tgtgtgaaat      480
tgttatccgc tcacaattcc acacaacata cgagccggaa gcataaagtg taaagcctgg      540
ggtgcctaat gagtgagcta actcacatta attgcgttgc gctcactgcc cgctttccag      600
tcgggaaacc tgtcgtgcca gctgcattaa tgaatcggcc aacgcgcggg gagaggcggt      660
ttgcgtattg ggcgctcttc cgcttcctcg ctcactgact cgctgcgctc ggtcgttcgg      720
ctgcggcgag cggtatcagc tcactcaaag gcggtaatac ggttatccac agaatcaggg      780
gataacgcag gaaagaacat gtgagcaaaa ggccagcaaa aggccaggaa ccgtaaaaag      840
gccgcgttgc tggcgttttt ccataggctc cgcccccctg acgagcatca caaaaatcga      900
cgctcaagtc agaggtggcg aaacccgaca ggactataaa gataccaggc gtttccccct      960
ggaagctccc tcgtgcgctc tcctgttccg accctgccgc ttaccggata cctgtccgcc     1020
tttctccctt cgggaagcgt ggcgctttct caatgctcac gctgtaggta tctcagttcg     1080
gtgtaggtcg ttcgctccaa gctgggctgt gtgcacgaac cccccgttca gcccgaccgc     1140
tgcgccttat ccggtaacta tcgtcttgag tccaacccgg taagacacga cttatcgcca     1200
ctggcagcag ccactggtaa caggattagc agagcgaggt atgtaggcgg tgctacagag     1260
```

-continued

```
ttcttgaagt ggtggcctaa ctacggctac actagaagga cagtatttgg tatctgcgct      1320
ctgctgaagc cagttacctt cggaaaaaga gttggtagct cttgatccgg caaacaaacc      1380
accgctggta gcggtggttt ttttgtttgc aagcagcaga ttacgcgcag aaaaaaagga      1440
tctcaagaag atcctttgat cttttctacg gggtctgacg ctcagtggaa cgaaaactca      1500
cgttaaggga ttttggtcat gagattatca aaaaggatct tcacctagat ccttttgggg      1560
tgggcgaaga actccagcat gagatccccg cgctggagga tcatccagcc ctgatagaaa      1620
cagaagccac tggagcacct caaaaacacc atcatacact aaatcagtaa gttggcagca      1680
tcacccgacg cactttgcgc cgaataaata cctgtgacgg aagatcactt cgcagaataa      1740
ataaatcctg gtgtccctgt tgataccggg aagccctggg ccaacttttg gcgaaaatga      1800
gacgttgatc ggcacgtaag aggttccaac tttcaccata atgaaataag atcactaccg      1860
ggcgtatttt ttgagttatc gagattttca ggagctgata gaaacagaag ccactggagc      1920
acctcaaaaa caccatcata cactaaatca gtaagttggc agcatcaccc gacgcacttt      1980
gcgccgaata aatacctgtg acggaagatc acttcgcaga ataaataaat cctggtgtcc      2040
ctgttgatac cgggaagccc tgggccaact tttggcgaaa atgagacgtt gatcggcacg      2100
taagaggttc caactttcac cataatgaaa taagatcact accgggcgta ttttttgagt      2160
tatcgagatt ttcaggagct ctttggcatc gtctctcgcc tgtcccctca gttcagtaat      2220
ttcctgcatt tgcctgtttc cagtcggtag atattccaca aaacagcagg gaagcagcgc      2280
ttttccgctg cataaccctg cttcggggtc attatagcga ttttttcggt atatccatcc      2340
tttttcgcac gatatacagg attttgccaa agggttcgtg tagactttcc ttggtgtatc      2400
caacggcgtc agccgggcag gataggtgaa gtaggcccac ccgcgagcgg gtgttccttc      2460
ttcactgtcc cttattcgca cctggcggtg ctcaacggga tcctgctct gcgaggctgg      2520 ccggctaccg ccggcgtaac agatgagggc aagcggatgg ctgatgaaac caagccaacc      2580
aggaagggca gcccacctat caaggtgtac tgccttccag acgaacgaag agcgattgag      2640
gaaaaggcgg cggcggccgg catgagcctg tcggcctacc tgctggccgt cggccagggc      2700
tacaaaatca cgggcgtcgt ggactatgag cacgtccgcg agggcgtccc ggaaaacgat      2760
tccgaagccc aacctttcat agaaggcggc ggtggaatcg aaatctcgtg atggcaggtt      2820
gggcgtcgct tggtcggtca tttcgaaaaa ggttaggaat acggttagcc atttgcctgc      2880
ttttatatag ttcantatgg gattcacctt tatgttgata agaaataaaa gaaaatgcca      2940
ataggatatc ggcattttct tttgcgtttt tatttgttaa ctgttaattg tccttgttca      3000
aggatgctgt ctttgacaac agatgttttc ttgcctttga tgttcagcag gaagctcggc      3060
gcaaacgttg attgtttgtc tgcgtagaat cctctgtttg tcatatagct tgtaatcacg      3120
acattgtttc ctttcgcttg aggtacagcg aagtgtgagt aagtaaaggt tacatcgtta      3180
ggcggatcaa gatccatttt taacacaagg ccagttttgt tcagcggctt gtatgggcca      3240
gttaaagaat tagaaacata accaagcatg taaatatcgt tagacgtaat gccgtcaatc      3300 gtcattttg atccgcggga gtcagtgaac aggtaccatt tgccgttcat tttaaagacg      3360
ttcgcgcgtt caatttcatc tgttactgtg ttagatgcaa tcagcggttt catcactttt      3420
ttcagtgtgt aatcatcgtt tagctcaatc ataccgagag cgccgtttgc taactcagcc      3480
gtgcgttttt tatcgctttg cagaagtttt tgactttctt gacggaagaa tgatgtgctt      3540
ttgccatagt atgctttgtt aaataaagat tcttcgcctt ggtagccatc ttcagttcca      3600
```

```
gtgtttgctt caaatactaa gtatttgtgg cctttatctt ctacgtagtg aggatctctc    3660
agcgtatggt tgtcgcctga gctgtagttg ccttcatcga tgaactgctg tacattttga    3720
tacgtttttc cgtcaccgtc aaagattgat ttataatcct ctacaccgtt gatgttcaaa    3780
gagctgtctg atgctgatac gttaacttgt gcagttgtca gtgtttgttt gccgtaatgt    3840
ttaccggaga aatcagtgta gaataaacgg atttttccgt cagatgtaaa tgtggctgaa    3900
cctgaccatt cttgtgtttg gtcttttagg atagaatcat ttgcatcgaa tttgtcgctg    3960
tctttaaaga cgcggccagc gttttttccag ctgtcaatag aagtttcgcc gactttttga    4020
tagaacatgt aaatcgatgt gtcatccgca ttttttaggat ctccggctaa tgcaaagacg    4080
atgtggtagc cgtgatagtt tgcgacagtg ccgtcagcgt tttgtaatgg ccagctgtcc    4140
caaacgtcca ggcctttgc agaagagata ttttttaattg tggacgaatc aaattcagaa    4200
acttgatatt tttcattttt ttgctgttca gggatttgca gcatatcatg gcgtgtaata    4260
tgggaaatgc cgtatgtttc cttatatggc ttttggttcg tttctttcgc aaacgcttga    4320
gttgcgcctc ctgccagcag tgcggtagta aaggttaata ctgttgcttg ttttgcaaac    4380
tttttgatgt tcatcgttca tgtctcctttt tttatgtact gtgttagcgg tctgcttctt    4440
ccagccctcc tgtttgaaga tggcaagtta gttacgcaca ataaaaaag acctaaaata    4500 tgtaaggggt gacgccaaag tatacacttt gcccttttaca cattttaggt cttgcctgct    4560
ttatcagtaa caaacccgcg cgatttactt ttcgacctca ttctattaga ctctcgtttg    4620
gattgcaact ggtctatttt cctcttttgt ttgatagaaa atcataaaag gatttgcaga    4680
ctacgggcct aaagaactaa aaaatctatc tgtttctttt cattctctgt attttttata    4740
gtttctgttg catgggcata aagttgcctt tttaatcaca attcagaaaa tatcataata    4800
tctcatttca ctaaataata gtgaacggca ggtatatgtg atgggttaaa aaggatcacc    4860
ccagagtccc gctcagaaga actcgtcaag aaggcgatag aaggcgatgc gctgcgaatc    4920
gggagcggcg ataccgtaaa gcacgaggaa gcggtcagcc cattcgccgc caagctcttc    4980
agcaatatca cgggtagcca acgctatgtc ctgatagcgg tccgccacac ccagccggcc    5040
acagtcgatg aatccagaaa agcggccatt ttccaccatg atattcggca agcaggcatc    5100
gccatgggtc acgacgagat cctcgccgtc gggcatccgc gccttgagcc tggcgaacag    5160
ttcggctggc gcgagcccct gatgctcttc gtccagatca tcctgatcga caagaccggc    5220
ttccatccga gtacgtgctc gctcgatgcg atgtttcgct tggtggtcga atgggcaggt    5280
agccggatca agcgtatgca gccgccgcat tgcatcagcc atgatggata ctttctcggc    5340
aggagcaagg tgagatgaca ggagatcctg ccccggcact cgcccaata gcagccagtc    5400 ccttcccgct tcagtgacaa cgtcgagaca gctgcgcaag aacgcccgt cgtggccagc    5460 cacgatagcc gcgctgcctc gtcttggagt tcattcaggg caccggacag gtcggtcttg    5520
acaaaaagaa ccgggcgccc ctgcgctgac agccggaaca cggcggcatc agagcagccg    5580
attgtctgtt gtgcccagtc atagccgaat agcctctcca cccaagcggc cggagaacct    5640
gcgtgcaatc catcttgttc aatcatgcga acgatcctc atcctgtctc ttgatcagat    5700
cttgatcccc tgcgccatca gatccttggc ggcaagaaag ccatccagtt tactttgcag    5760
ggcttcccaa ccttaccaga gggcgcccca gctggcaatt ccg                      5803
```

<210> SEQ ID NO 33
<211> LENGTH: 127
<212> TYPE: PRT
<213> ORGANISM: Artificial Sequence

```
<220> FEATURE:
<223> OTHER INFORMATION: General formula 1
<220> FEATURE:
<221> NAME/KEY: MISC_FEATURE
<222> LOCATION: (1)..(1)
<223> OTHER INFORMATION: Xaa is N or S.
<220> FEATURE:
<221> NAME/KEY: MISC_FEATURE
<222> LOCATION: (9)..(9)
<223> OTHER INFORMATION: Xaa is A or E.
<220> FEATURE:
<221> NAME/KEY: MISC_FEATURE
<222> LOCATION: (73)..(73)
<223> OTHER INFORMATION: Xaa is Y or C.

<400> SEQUENCE: 33

Xaa Asn His Gly Gly Asp Ala Thr Xaa Phe Met Asn Lys Val Lys Asn
1               5                   10                  15

Lys Glu Asp Gly Val Arg Leu Met Gly Phe Gly His Arg Val Tyr Lys
            20                  25                  30

Asn Tyr Asp Pro Arg Ala Ala Ile Val Lys Glu Thr Ala His Glu Ile
        35                  40                  45

Leu Glu His Leu Gly Gly Asp Asp Leu Leu Asp Leu Ala Ile Lys Leu
    50                  55                  60

Glu Glu Ile Ala Leu Ala Asp Asp Xaa Phe Ile Ser Arg Lys Leu Tyr
65                  70                  75                  80

Pro Asn Val Asp Phe Tyr Thr Gly Leu Ile Tyr Arg Ala Met Gly Phe
            85                  90                  95

Pro Thr Asp Phe Phe Thr Val Leu Phe Ala Ile Gly Arg Leu Pro Gly
            100                 105                 110

Trp Ile Ala His Tyr Arg Glu Gln Leu Gly Ala Ala Gly Asn His
            115                 120                 125
```